(12) United States Patent
Bly

(10) Patent No.: US 8,048,622 B2
(45) Date of Patent: Nov. 1, 2011

(54) IDENTIFYING INCREASED SUSCEPTIBILITY TO SCHIZOPHRENIA

(75) Inventor: Michael Bly, Ypsilanti, MI (US)

(73) Assignee: The Regents of the University of Michigan, Ann Arbor, MI (US)

( * ) Notice: Subject to any disclaimer, the term of this patent is extended or adjusted under 35 U.S.C. 154(b) by 967 days.

(21) Appl. No.: 11/451,204

(22) Filed: Jun. 12, 2006

(65) Prior Publication Data

US 2007/0009940 A1    Jan. 11, 2007

Related U.S. Application Data

(60) Provisional application No. 60/689,284, filed on Jun. 10, 2005.

(51) Int. Cl.
*C12Q 1/68* (2006.01)
*C12P 19/34* (2006.01)

(52) U.S. Cl. .............................. 435/6; 435/91.1; 436/63

(58) Field of Classification Search ........................ None
See application file for complete search history.

(56) References Cited

U.S. PATENT DOCUMENTS 7,736,852 B2 * 6/2010 Berrettini et al. .................. 435/6

OTHER PUBLICATIONS

Lohoff et al. (Neuropsychopharmacology, vol. 31, pp. 2739-2747, 2006).*
Richards et al. (Behavioral and Brain Functions, 2006, vol. 2, No. 39, pp. 1-6).*
Chen et al. (Schizophrenia Research, 2007, vol. 90, pp. 363-365, 2007).*
Ionnidis (Plost Med, 2005, 2(8):e124).*
Newton-Cheh (Mutation Research 2005, 573, pp. 54-69).*
Iwasa et al. (J Human Genet (2001) vol. 46:549-552).*
Tate et al. (Nature Genetics Supplement, Nov. 2004, vol. 11, pp. S43-S42).*
Blouin, et al., "Schizophrenia susceptibility loci on chromosomes 13q32 and 8p21", Nature Genetics (1998) pp. 70-73, vol. 20.
Brzustowicz, et al., "Linkage of Familial Schizophrenia to Chromosome 13q32", Am. J. Hum. Gen. (1999) pp. 1096-1103, vol. 65.
Erickson, et al., "Distinct pharmacological properties and distribution in neurons and endocrine cells of two isoforms of the human vesicular monoamine transporter", Proc. Natl. Acad. Sci. U. S. A. (1996) pp. 5166-5171, vol. 93.
Gurling, et al., "Genomewide Genetic Linkage Analysis Confirms the Presence of Susceptibility Loci for Schizophrenia, on Chromosomes 1q32.2, 5q33.2, and 8p21-22 and Provides Support for Linkage to Schizophrenia, on Chromosomes 11q23.3-24 and 20q12.1-11.23", Am. J. Hum. Genet. (2001) pp. 661-673, vol. 68.
Bly, "Mutation in the vesicular monoamine gene, SLC18A1, associated with schizophrenia", Schizophrenia Research (2005) pp. 337-338, vol. 78.
Hayashi, et al., "Vesicular Monoamine Transporter 1 Is Responsible for Storage of 5-Hydroxytryptamine in Rat Pinealocytes", J. Neurochem. (1999) pp. 2538-2545, vol. 73.
Woolley and Shaw, "A Biochemical and Pharmacological Suggestion About Certain Mental Disorders", PNAS (1954) pp. 228-231, vol. 40.
Schwab, et al.,"A genome-wide autosomal screen for schizophrenia susceptibility loci in 71 families with affected siblings: support for loci on chromosome 10p and 6.", Molecular Psychiatry, (2000) pp. 638-649, vol. 5.
Levinson, et al., "Multicenter Linkage Study of Schizophrenia Candidate Regions on Chromosomes 5q, 6q, 10p, and 13q: Schizophrenia Linkage Collaborative Group III", Am. J. Hum. Genet. (2000) pp. 652-663, vol. 67.

* cited by examiner

*Primary Examiner* — Sarae Bausch
(74) *Attorney, Agent, or Firm* — Casimir Jones, S.C.

(57) ABSTRACT

The present invention provides diagnostic markers of neuropsychiatric disorders (e.g., schizophrenia, schizoaffective disorder or serious mood disorders including bipolar disorder and recurrent unipolar disorder) for use in diagnosis, drug screening, therapy monitoring, research and therapeutic applications. In particular, the present invention provides SLC18A1 and TAAR2, and mutations therein, as biomarkers of neuropsychiatric disorders.

3 Claims, 2 Drawing Sheets

FIGURE 1

A. Human SLC18A1 Nucleic Acid Sequence (SEQ ID NO:5)

```
CACACACACACATACACAGAATCCTCAGATAACAGGAGGCAATAAATCCAACAGCACATCCACGTTCAGA
GAACAGTGTCCCTGCTGTCTTGCTAACAGCTGCCAATACCTCACTGAGTGCCTCACACCAACATGGGCTC
CAAGTGAGTTTCCTTCGTCTGGGCAGACTCCCTCCCCTCTTCCATAAAGGCTGCAGGAGACCTGTAGCTG
TCACAGGACCTTCCCTAAGAGCCCGCAGGGAAAGACTGCCCCAGTCCGGCCATCACCATGCTCCGGACCA
TTCTGGATGCTCCCCAGCGGTTGCTGAAGGAGGGGAGAGCGTCCCGGCAGCTGGTGCTGGTGGTGGTATT
CGTCGCTTTGCTCCTGGACAACATGCTGTTTACTGTGGTGGTGCCAATTGTGCCCACCTTCCTATATGAC
ATGGAGTTCAAAGAAGTCAACTCTTCTCTGCACCTCGGCCATGCCGGAAGTTCCCCACATGCCCTCGCCT
CTCCTGCCTTTTCCACCATCTTCTCCTTCTTCAACAACAACACCGTGGCTGTTGAAGAAAGCGTACCTAG
TGGAATAGCATGGATGAATGACACTGCCAGCACCATCCCACCTCCAGCCACTGAAGCCATCTCAGCTCAT
AAAAACAACTGCTTGCAAGGCACAGGTTTCTTGGAGGAAGAGATTACCCGGGTCGGGGTTCTGTTTGCTT
CAAAGGCTGTGATGCAACTTCTGGTCAACCCATTCGTGGGCCCTCTCACCAACAGGATTGGATATCATAT
CCCCATGTTTGCTGGCTTTGTTATCATGTTTCTCTCCACAGTTATGTTTGCTTTTTCTGGGACCTATACT
CTACTCTTTGTGGCCCGAACCCTTCAAGGCATTGGATCTTCATTTTCATCTGTTGCAGGTCTTGGAATGC
TGGCCAGTGTCTACACTGATGACCATGAGAGAGGACGAGCCATGGGAACTGCTCTGGGGGGCCTGGCCTT
GGGGTTGCTGGTGGGAGCTCCCTTTGGAAGTGTAATGTACGAGTTTGTTGGGAAGTCTGCACCCTTCCTC
ATCCTGGCCTTCCTGGCACTACTGGATGGAGCACTCCAGCTTTGCATCCTACAGCCTTCCAAAGTCTCTC
CTGAGAGTGCCAAGGGGACTCCCCTCTTTATGCTTCTCAAAGACCCTTACATCCTGGTGGCTGCAGGGTC
CATCTGCTTTGCCAACATGGGGGTGGCCATCCTGGAGCCCACACTGCCCATCTGGATGATGCAGACCATG
TGCTCCCCCAAGTGGCAGCTGGGTCTAGCTTTCTTGCCTGCCAGTGTGTCCTACCTCATTGGCACCAACC
TCTTTGGTGTGTTGGCCAACAAGATGGGTCGGTGGCTGTGTTCCCTAATCGGGATGCTGGTAGTAGGTAC
CAGCTTGCTCTGTGTTCCTCTGGCTCACAATATTTTGGTCTCATTGGCCCCAATGCAGGGCTTGGCCTT
GCCATAGGCATGGTGGATTCTTCTATGATGCCCATCATGGGGCACCTGGTGGATCTACGCCACACCTCGG
TGTATGGGAGTGTCTACGCCATCGCTGATGTGGCTTTTTGCATGGGCTTTGCTATAGGTCCATCCACCGG
TGGTGCCATTGTAAAGGCCATCGGTTTTCCTGGCTCATGGTCATCACTGGGGTCATCAACATCGTCTAT
GCTCCACTCTGCTACTACCTGCGGAGCCCCCCGGCAAAGGAAGAGAAGCTTGCTATTCTGAGTCAGGACT
GCCCCATGGAGACCCGGATGTATGCAACCCAGAAGCCCACGAAGGAATTCCTCTGGGGGAGGACAGTGA
TGAGGAGCCTGACCATGAGGAGTAGCAGCAGAAGGTGCTCCTTGAATTCATGATGCCTCAGTGACCACCT
CTTTCCCTGGGACCAGATCACCATGGCTGAGCCCACGGCTCAGTGGGCTTCACATACCTCTGCCTGGGAA
TCTTCTTTCCTCCCCTCCCATGGACACTGTCCCTGATACTCTTCTCACCTGTGTAACTTGTAGCTCTTCC
TCTATGCCTTGGTGCCGCAGTGGCCCATCTTTATGGGAAGACAGAGTGATGCACCTTCCCGCTGCTGTG
AGGTTGATTAAACTTGAGCTGTGACGGGTTCTGCAAGGGGTGACTCATTGCATAGAGGTGGTAGTGAGTA
ATGTGCCCCTGAAACCAGTGGGGTGACTGACAAGCCTCTTTAATCTGTTGCCTGATTTTCTCTGGCATAG
TCCCAACAGATCGGAAGAGTGTTACCCTCTTTTCCTCAACGTGTTCTTTCCCGGGTTTTCCCAGCCGAGT
TGAGAAAATGTTCTCAGCATTGTCTTGCTGCCAAATGCCAGCTTGAAGAGTTTTGTTTTGTTTTTTTTCC
ATTTATTTTTTTTTTAATAAAGTGAGTGATTTTCTGTGGCTAAATCTAGAGCTGCTAAAAGGGCTTT
ACCCTCAGTGAAAAGTGTCTTCTATTTTCATTATCTTTCAGAAACAGGAGCCCATTTCTCTTCTGCTGGA
GTTATTGACATTCTCCTGACCTCCCCTGTGTGTTCCTACCTTTTCTGAACCTCTTAGACTCTTAGAAATA
AAAGTAGAAGAAAGACAGAAAAAATAACTGATTAGACCCAAGATTTCATGGGAAGAAGTTAAAAGAAACT
GCCTTGAAATCCCTCCTGATTGTAGATTTCCTAATAGGAGGGGTGTAATGTGACATTGTTCATACTTGCT
AATAAATACATTATTGCCT
```

B. Human SLC18A1 Amino Acid Sequence (SEQ ID NO:6)

```
MLRTILDAPQRLLKEGRASRQLVLVVVFVALLLDNMLFTVVVPIVPTFLYDMEFKEVNSSLHLGHAGSSPH
ALASPAFSTIFSFFNNNTVAVEESVPSGIAWMNDTASTIPPPATEAISAHKNNCLQGTGFLEEEITRVGVL
FASKAVMQLLVNPFVGPLTNRIGYHIPMFAGFVIMFLSTVMFAFSGTYTLLFVARTLQGIGSSFSSVAGLG
MLASVYTDDHERGRAMGTALGGLALGLLVGAPFGSVMYEFVGKSAPFLILAFLALLDGALQLCILQPSKVS
PESAKGTPLFMLLKDPYILVAAGSICFANMGVAILEPTLPIWMMQTMCSPKWQLGLAFLPASVSYLIGTNL
FGVLANKMGRWLCSLIGMLVVGTSLLCVPLAHNIFGLIGPNAGLGLAIGMVDSSMMPIMGHLVDLRHTSVY
GSVYAIADVAFCMGFAIGPSTGGAIVKAIGFPWLMVITGVINIVYAPLCYYLRSPPAKEEKLAILSQDCPM
ETRMYATQKPTKEFPLGEDSDEEPDHEE
```

FIGURE 2

A.  Human TAAR2 Nucleic Acid Sequence (SEQ ID NO:7)

ATGTATTCATTTATGGCAGGATCCATATTCATCACAATATTTGGCAATCTTGCCATGATAATTTCCATTT
CCTACTTCAAGCAGCTTCACACACCAACCAACTTCCTCATCCTCTCCATGGCCATCACTGATTTCCTCCT
GGGATTCACCATCATGCCATATAGTATGATCAGATCGGTGGAGAACTGCTGGTATTTGGGCTTACATTT
TGCAAGATTTATTATAGTTTTGACCTGATGCTTAGCATAACATCCATTTTTCATCTTTGCTCAGTGGCCA
TTGATAGATTTTATGCTATATGTTACCCATTACTTTATTCCACCAAAATAACTATTCCAGTCATTAAAAG
ATTGCTACTTCTATGTTGGTCGGTCCCTGGAGCATTTGCCTTCGGGGTGGTCTTCTCAGAGGCCTATGCA
GATGGAATAGAGGGCTATGACATCTTGGTTGCTTGTTCCAGTTCCTGCCCAGTGATGTTCAACAAGCTAT
GGGGGACCACCTTGTTTATGGCAGGTTTCTTCACTCCTGGGTCTATGATGGTGGGGATTTATGGCAAAAT
TTTTGCAGTATCCAGAAAACATGCTCATGCCATCAATAACTTGCGAGAAAATCAAAATAATCAAGTGAAG
AAAGACAAAAAAGCTGCCAAAACTTTAGGAATAGTGATAGGAGTTTTCTTATTATGTTGGTTTCCTTGTT
TCTTCACAATTTTATTGGATCCCTTTTGAACTTCTCTACTCCTGTAGTTTTGTTTGATGCCTTGACATG
GTTTGGCTATTTTAACTCCACATGTAATCCGTTAATATATGGTTTCTTCTATCCCTGGTTTCGCAGAGCA
CTGAAGTACATTTTGCTAGGTAAAATTTTCAGCTCATGTTTCCATAATACTATTTTGTGTATGCAAAAAG
AAAGTGAGTAG

B.  Human TAAR2 Amino Acid Sequence (SEQ ID NO:8)

MYSFMAGSIFITIFGNLAMIISISYFKQLHTPTNFLILSMAITDFLLGFTIMPYSMIRSVENCWYFGLTFC
KIYYSFDLMLSITSIFHLCSVAIDRFYAICYPLLYSTKITIPVIKRLLLLCWSVPGAFAFGVVFSEAYADG
IEGYDILVACSSSCPVMFNKLWGTTLFMAGFFTPGSMMVGIYGKIFAVSRKHAHAINNLRENQNNQVKKDK
KAAKTLGIVIGVFLLCWFPCFFTILLDPFLNFSTPVVLFDALTWFGYFNSTCNPLIYGFFYPWFRRALKYI
LLGKIFSSCFHNTILCMQKESE

IDENTIFYING INCREASED SUSCEPTIBILITY TO SCHIZOPHRENIA

The present application claims priority to U.S. Provisional Application Ser. No. 60/689,284, filed Jun. 10, 2005, herein incorporated by reference.

FIELD OF THE INVENTION

The present invention provides diagnostic markers of neuropsychiatric disorders (e.g., schizophrenia, schizoaffective disorder or serious mood disorders including bipolar disorder and recurrent unipolar disorder) for use in diagnosis, drug screening, therapy monitoring, research and therapeutic applications. In particular, the present invention provides SLC18A1 and TAAR2, and mutations therein, as biomarkers of neuropsychiatric disorders.

BACKGROUND OF THE INVENTION

Historically, schizophrenia (SZ) and bipolar (BP) disorder have been considered as non-overlapping nosological entities, with distinctive clinical characteristics, unique treatment regimens and separate (albeit unknown) etiologies.

The schizophrenic disorders are a group of syndromes manifested by massive disruption of thinking, mood, and overall behavior as well as poor filtering of stimuli. Diagnosis of schizophrenic disorder is currently based upon the presence of a number of behavioral characteristics of at least six months duration including: slowly progressive social withdrawal usually often accompanied by a deterioration in personal care; loss of ego boundaries with the inability to perceive oneself as a separate entity; loose thought associations, often with slowed thinking or overinclusive and rapid shifting from topic to topic; autistic absorption in inner thoughts and frequent sexual or religious preoccupations; auditory hallucinations, often of a derogatory nature; and delusions, frequently of grandiose or persecutory nature. Frequent additional signs include: flat effect and rapidly alternating mood shift irrespective of circumstances; hypersensitivity to environmental stimuli, with a feeling of enhanced sensory awareness; variability or changeable behavior incongruent with the external environment; concrete thinking with the inability to abstract; inappropriate symbolism; impaired concentration worsened by hallucinations and delusions; and depersonalization, wherein one behaves like a detached observer of one's own actions. Diagnosis of a schizophrenic disorder based upon these behaviors can thus be quite arbitrary and is influenced by sociocultural factors and schools of psychiatric thought. At present, there is no laboratory method (e.g., molecular diagnostic) for diagnosis or confirmation of a diagnosis of schizophrenia.

Bipolar disorder, also known as manic-depressive illness, involves cycles of mania and depression. Signs and symptoms of mania include: extreme irritability and distractibility; excessive euphoric feelings; a sustained period of behavior that is different from the usual behavior; increased energy activity, restlessness, racing thoughts and rapid talking; decreased need for sleep; unrealistic beliefs in one's abilities and powers; uncharacteristically poor judgment; increased sexual drive; abuse of drugs, particularly cocaine, alcohol and sleeping medications; obnoxious, provocative or intrusive behavior and denial that anything is wrong. Signs and symptoms of depression include: persistent sad, anxious or empty mood; feeling of hopelessness or pessimism; feeling of guilt, worthlessness or helplessness; loss of interest or pleasure in ordinary activities; decreased energy, a feeling of fatigue or of being "slowed down"; difficulty concentrating, remembering and making decisions; restlessness and irritability; sleep disturbances; loss of appetite and weight, or weight gain; chronic pain or other persistent bodily symptoms that are not caused by physical disease; and thoughts of death or suicide. Most people with manic-depressive illness can be helped with treatment. However, manic-depressive illness, which is currently diagnosed by symptoms alone, is often not recognized by the patient, relatives, friends and even physicians. If left untreated, bipolar disorder tends to worsen, and the person experiences episodes of full-fledged mania and clinical depression.

Accordingly, a great need exists for better, more definitive diagnostic markers and methods for diagnosing neuropsychiatric disorders including schizophrenia and bipolar disorder and other related disorders.

SUMMARY OF THE INVENTION

The present invention provides diagnostic markers of neuropsychiatric disorders (e.g., schizophrenia, schizoaffective disorder or serious mood disorders including bipolar disorder and recurrent unipolar disorder) for use in diagnosis, drug screening, therapy monitoring, research and therapeutic applications. In particular, the present invention provides SLC18A1 and TAAR2, and mutations therein, as biomarkers of neuropsychiatric disorders.

In some embodiments, the present invention provides methods for detecting a disorder (e.g., neuropsychiatric disorder) in a subject comprising detecting SLC18A1 and/or TAAR2 nucleic acid sequence in a sample from the subject. In certain embodiments, the detecting comprises determining the presence or absence of SEQ ID NOS. 2 and/or 4, or other alleles found to correlate with a neuropsychiatric disorder. In particular embodiments, the subject is a human. In further embodiments, the neuropsychiatric disorder is schizophrenia.

In certain embodiments, the present invention provides methods for selecting a therapeutic course of action, comprising: a) detecting the presence or absence of SEQ ID NOS. 2 and/or 4 in a sample from a subject suspected of having a neuropsychiatric disorder; and b) treating the subject with a therapeutic compound or intervention based on the presence of absence of SEQ ID NOS. 2 and/or 4 in the sample, or other allele found to correlate with a neuropsychiatric disorder.

In additional embodiments, the present invention provides methods for identifying and treating a subject, comprising: a) detecting a neuropsychiatric disease in a subject by detecting the presence of SEQ ID NO. 2 and/or 4 (or other allele found to correlate with the neuropsychiatric disease) in a sample from the subject; and b) treating the subject with a therapy that is selected based on the detecting step.

DESCRIPTION OF THE FIGURES

FIG. 1A shows the wild type nucleic acid sequence of human SLC18A1 (SEQ ID NO: 5), and FIG. 1B shows the wild-type amino acid sequence of human SLC18A1 (SEQ ID NO: 6).

FIG. 2A shows the wild type nucleic acid sequence of human TAAR2 (SEQ ID NO: 7), and FIG. 2B shows the wild-type amino acid sequence of human TAAR2 (SEQ ID NO: 8).

DETAILED DESCRIPTION OF THE INVENTION

Experiments conducted during development of the present invention suggested that neuropsychiatric disease (e.g., schizophrenia) could be caused by and correlates to mutations in a gene encoding the transport of serotonin (e.g., SLC18A1). A search was made to find a gene within a neuropsychiatric disease genetically susceptible region, 8p (Blouin, et al., 1998. Nat. Genet. 20, 70-73; Brzustowicz et al., 2001. Am. J. Hum. Gen. 1999. 65, 1096-1103; Erickson et al., 1996. Proc. Natl. Acad. Sci. U.S.A. 93, 96 5166-5171; Gurling et al., 2001. Am. J. Hum. Genet. 68, 661-673). SLC18A1 was identified a candidate (See e.g., Examples 1 and 2). SLC18A1 is solute carrier family 18 (vesicular monoamine), member 1 (See, e.g., Genbank Accession number NM_003053 for the nucleotide and amino acid sequences, and for additional information). This gene contains 18 exons and predicts a protein of 525 amino acids. The predicted secondary structure contains twelve putative transmembrane domains (Hayashi et al., 1995. Proc. Natl. Acad. Sci. U.S.A. 40, 228-231). SLC18A1 has been shown to be abundantly expressed in the human adrenal medulla (Hayashi et al., 1999). In rat pinealocytes, the vesicular monoamine transporter has been implicated to be responsible for storage of serotonin (Woolley and Shaw, 1954). Mutations within the SLC18A1 gene were associated with neuropsychiatric disorders (See, e.g., Examples 1 and 2).

During further searches of a susceptible region for neuropsychiatric disorders (e.g., schizophrenia) in locus 6q (See, e.g., Schwab et al., Molecular Psychiatry 2000; 5: 638-649; Levinson et al., Am. J. Hum. Genet. 2000; 67: 652-663; Schwab et al., Molecular Psychiatry 2000; 5: 638-649; and Example 1), TAAR2 was identified as a candidate gene. TAAR2, also known as GPR58, is a G protein-coupled receptor 58. This gene contains one exon and predicts a protein of 306 amino acids. The predicted secondary structure contains 7 putative transmembrane domains. Mutations within the TAAR2 gene were associated with neuropsychiatric disorders (See, e.g., Examples 1 and 3).

Accordingly, the present invention provides diagnostic markers of neuropsychiatric disorders (e.g., schizophrenia, schizoaffective disorder or serious mood disorders including bipolar disorder and recurrent unipolar disorder) for use in diagnosis, drug screening, therapy monitoring, research and therapeutic applications. In particular, the present invention provides SLC18A1 and TAAR2, and mutations therein, as biomarkers of neuropsychiatric disorders.

I. Detection of SLC18A1 and TAAR2 Alleles

In some embodiments, the present invention provides methods of detecting the presence of wild type or variant (e.g., mutant or polymorphic) SLC18A1 nucleic acids or polypeptides and TAAR2 nucleic acids and polypeptides. The detection of mutant SLC18A1 nucleic acids and polypeptides and TAAR2 nucleic acids and polypeptides finds use in the diagnosis of disease (e.g., neuropsychiatric disorders such as schizophrenia, bipolar disorder and other related disorders).

A. SLC18A1 and TAAR2 Alleles

In some embodiments, the present invention includes alleles of SLC18A1 and TAAR2 that increase a patient's susceptibility to neuropsychiatric disorders such as schizophrenia (e.g., including, but not limited to, SEQ ID NOs: 2 and 4, also see Examples 2 and 3). However, the present invention is not limited to the mutations described in SEQ ID NOs: 2 and 4. Any mutation that results in the undesired phenotype (e.g., neuropsychiatric disease) is within the scope of the present invention.

B. Detection of SLC18A1 and TAAR2 Alleles

Accordingly, the present invention provides methods for determining whether a patient has an increased susceptibility to neuropsychiatric disease by determining whether the individual has a variant SLC18A1 allele or TAAR2 allele, respectively. In other embodiments, the present invention provides methods for providing a prognosis of increased risk for neuropsychiatric disease to an individual based on the presence or absence of one or more variant alleles of SLC18A1 or TAAR2. In preferred embodiments, the variation causes a truncation or other mutation of the SLC18A1 or TAAR2 protein.

A number of methods are available for analysis of variant (e.g., mutant or polymorphic) nucleic acid sequences. Assays for detection variants (e.g., polymorphisms or mutations) fall into several categories, including, but not limited to direct sequencing assays, fragment polymorphism assays, hybridization assays, and computer based data analysis. Protocols and commercially available kits or services for performing multiple variations of these assays are available. In some embodiments, assays are performed in combination or in hybrid (e.g., different reagents or technologies from several assays are combined to yield one assay). The following assays are useful in the present invention.

1. Direct Sequencing Assays

In some embodiments of the present invention, variant sequences are detected using a direct sequencing technique. In these assays, DNA samples are first isolated from a subject using any suitable method. In some embodiments, the region of interest is cloned into a suitable vector and amplified by growth in a host cell (e.g., a bacteria). In other embodiments, DNA in the region of interest is amplified using PCR.

Following amplification, DNA in the region of interest (e.g., the region containing the SNP or mutation of interest) is sequenced using any suitable method, including but not limited to manual sequencing using radioactive marker nucleotides, or automated sequencing. The results of the sequencing are displayed using any suitable method. The sequence is examined and the presence or absence of a given SNP or mutation is determined.

2. PCR Assay

In some embodiments of the present invention, variant sequences are detected using a PCR-based assay. In some embodiments, the PCR assay comprises the use of oligonucleotide primers that hybridize only to the variant or wild type allele of SLC18A1 or TAAR2 (e.g., to the region of polymorphism or mutation). Both sets of primers are used to amplify a sample of DNA. If only the mutant primers result in a PCR product, then the patient has the mutant SLC18A1 allele or mutant TAAR2 allele. If only the wild-type primers result in a PCR product, then the patient has the wild type allele of SLC18A1 or TAAR2.

3. Mutational Detection by dHPLC

In some embodiments of the present invention, variant sequences are detected using a PCR-based assay with consecutive detection of nucleotide variants by dHPLC (denaturing high performance liquid chromatography). Exemplary systems and Methods for dHPLC include, but are not limited to, WAVE (Transgenomic, Inc; Omaha, Nebr.) or VARIAN equipment (Palo Alto, Calif.).

4. Fragment Length Polymorphism Assays

In some embodiments of the present invention, variant sequences are detected using a fragment length polymorphism assay. In a fragment length polymorphism assay, a unique DNA banding pattern based on cleaving the DNA at a series of positions is generated using an enzyme (e.g., a restriction enzyme or a CLEAVASE I (Third Wave Technologies, Madison, Wis.) enzyme). DNA fragments from a sample containing a SNP or a mutation will have a different banding pattern than wild type.

a. RFLP Assay

In some embodiments of the present invention, variant sequences are detected using a restriction fragment length polymorphism assay (RFLP). The region of interest is first isolated using PCR. The PCR products are then cleaved with restriction enzymes known to give a unique length fragment for a given polymorphism. The restriction-enzyme digested PCR products are separated by agarose gel electrophoresis and visualized by ethidium bromide staining. The length of the fragments is compared to molecular weight markers and fragments generated from wild-type and mutant controls.

b. CFLP Assay

In other embodiments, variant sequences are detected using a CLEAVASE fragment length polymorphism assay (CFLP; Third Wave Technologies, Madison, Wis.; See e.g., U.S. Pat. Nos. 5,843,654; 5,843,669; 5,719,208; and 5,888,780; each of which is herein incorporated by reference). This assay is based on the observation that when single strands of DNA fold on themselves, they assume higher order structures that are highly individual to the precise sequence of the DNA molecule. These secondary structures involve partially duplexed regions of DNA such that single stranded regions are juxtaposed with double stranded DNA hairpins. The CLEAVASE I enzyme, is a structure-specific, thermostable nuclease that recognizes and cleaves the junctions between these single-stranded and double-stranded regions.

The region of interest is first isolated, for example, using PCR. Then, DNA strands are separated by heating. Next, the reactions are cooled to allow intrastrand secondary structure to form. The PCR products are then treated with the CLEAVASE I enzyme to generate a series of fragments that are unique to a given SNP or mutation. The CLEAVASE enzyme treated PCR products are separated and detected (e.g., by agarose gel electrophoresis) and visualized (e.g., by ethidium bromide staining). The length of the fragments is compared to molecular weight markers and fragments generated from wild-type and mutant controls.

5. Hybridization Assays

In preferred embodiments of the present invention, variant sequences are detected a hybridization assay. In a hybridization assay, the presence of absence of a given SNP or mutation is determined based on the ability of the DNA from the sample to hybridize to a complementary DNA molecule (e.g., a oligonucleotide probe). A variety of hybridization assays using a variety of technologies for hybridization and detection are available. A description of a selection of assays is provided below.

a. Direct Detection of Hybridization

In some embodiments, hybridization of a probe to the sequence of interest (e.g., a SNP or mutation) is detected directly by visualizing a bound probe (e.g., a Northern or Southern assay; See e.g., Ausabel et al. (eds.), Current Protocols in Molecular Biology, John Wiley & Sons, NY (1991)). In a these assays, genomic DNA (Southern) or RNA (Northern) is isolated from a subject. The DNA or RNA is then cleaved with a series of restriction enzymes that cleave infrequently in the genome and not near any of the markers being assayed. The DNA or RNA is then separated (e.g., on an agarose gel) and transferred to a membrane. A labeled (e.g., by incorporating a radionucleotide) probe or probes specific for the SNP or mutation being detected is allowed to contact the membrane under a condition or low, medium, or high stringency conditions. Unbound probe is removed and the presence of binding is detected by visualizing the labeled probe.

b. Detection of Hybridization Using "DNA Chip" Assays

In some embodiments of the present invention, variant sequences are detected using a DNA chip hybridization assay. In this assay, a series of oligonucleotide probes are affixed to a solid support. The oligonucleotide probes are designed to be unique to a given SNP or mutation. The DNA sample of interest is contacted with the DNA "chip" and hybridization is detected.

In some embodiments, the DNA chip assay is a GeneChip (Affymetrix, Santa Clara, Calif.; See e.g., U.S. Pat. Nos. 6,045,996; 5,925,525; and 5,858,659; each of which is herein incorporated by reference) assay. The GeneChip technology uses miniaturized, high-density arrays of oligonucleotide probes affixed to a "chip." Probe arrays are manufactured by Affymetrix's light-directed chemical synthesis process, which combines solid-phase chemical synthesis with photolithographic fabrication techniques employed in the semiconductor industry. Using a series of photolithographic masks to define chip exposure sites, followed by specific chemical synthesis steps, the process constructs high-density arrays of oligonucleotides, with each probe in a predefined position in the array. Multiple probe arrays are synthesized simultaneously on a large glass wafer. The wafers are then diced, and individual probe arrays are packaged in injection-molded plastic cartridges, which protect them from the environment and serve as chambers for hybridization.

The nucleic acid to be analyzed is isolated, amplified by PCR, and labeled with a fluorescent reporter group. The labeled DNA is then incubated with the array using a fluidics station. The array is then inserted into the scanner, where patterns of hybridization are detected. The hybridization data are collected as light emitted from the fluorescent reporter groups already incorporated into the target, which is bound to the probe array. Probes that perfectly match the target generally produce stronger signals than those that have mismatches. Since the sequence and position of each probe on the array are known, by complementarity, the identity of the target nucleic acid applied to the probe array can be determined.

In other embodiments, a DNA microchip containing electronically captured probes (Nanogen, San Diego, Calif.) is utilized (See e.g., U.S. Pat. Nos. 6,017,696; 6,068,818; and 6,051,380; each of which are herein incorporated by reference). Through the use of microelectronics, Nanogen's technology enables the active movement and concentration of charged molecules to and from designated test sites on its semiconductor microchip. DNA capture probes unique to a given SNP or mutation are electronically placed at, or "addressed" to, specific sites on the microchip. Since DNA has a strong negative charge, it can be electronically moved to an area of positive charge.

First, a test site or a row of test sites on the microchip is electronically activated with a positive charge. Next, a solution containing the DNA probes is introduced onto the microchip. The negatively charged probes rapidly move to the positively charged sites, where they concentrate and are chemically bound to a site on the microchip. The microchip is then washed and another solution of distinct DNA probes is added until the array of specifically bound DNA probes is complete.

A test sample is then analyzed for the presence of target DNA molecules by determining which of the DNA capture probes hybridize, with complementary DNA in the test sample (e.g., a PCR amplified gene of interest). An electronic charge is also used to move and concentrate target molecules to one or more test sites on the microchip. The electronic concentration of sample DNA at each test site promotes rapid hybridization of sample DNA with complementary capture probes (hybridization may occur in minutes). To remove any unbound or nonspecifically bound DNA from each site, the polarity or charge of the site is reversed to negative, thereby forcing any unbound or nonspecifically bound DNA back into solution away from the capture probes. A laser-based fluorescence scanner is used to detect binding, In still further embodiments, an array technology based upon the segregation of fluids on a flat surface (chip) by differences in surface tension (ProtoGene, Palo Alto, Calif.) is utilized (See e.g., U.S. Pat. Nos. 6,001,311; 5,985,551; and 5,474,796; each of which is herein incorporated by reference). Protogene's technology is based on the fact that fluids can be segregated on a flat surface by differences in surface tension that have been imparted by chemical coatings. Once so segregated, oligonucleotide probes are synthesized directly on the chip by ink-jet printing of reagents. The array with its reaction sites defined by surface tension is mounted on a X/Y translation stage under a set of four piezoelectric nozzles, one for each of the four standard DNA bases. The translation stage moves along each of the rows of the array and the appropriate reagent is delivered to each of the reaction site. For example, the A amidite is delivered only to the sites where amidite A is to be coupled during that synthesis step and so on. Common reagents and washes are delivered by flooding the entire surface and then removing them by spinning.

DNA probes unique for the SNP or mutation of interest are affixed to the chip using Protogene's technology. The chip is then contacted with the PCR-amplified genes of interest. Following hybridization, unbound DNA is removed and hybridization is detected using any suitable method (e.g., by fluorescence de-quenching of an incorporated fluorescent group).

In yet other embodiments, a "bead array" is used for the detection of polymorphisms (Illumina, San Diego, Calif.; See e.g., PCT Publications WO 99/67641 and WO 00/39587, each of which is herein incorporated by reference). Illumina uses a BEAD ARRAY technology that combines fiber optic bundles and beads that self-assemble into an array. Each fiber optic bundle contains thousands to millions of individual fibers depending on the diameter of the bundle. The beads are coated with an oligonucleotide specific for the detection of a given SNP or mutation. Batches of beads are combined to form a pool specific to the array. To perform an assay, the BEAD ARRAY is contacted with a prepared subject sample (e.g., DNA). Hybridization is detected using any suitable method.

c. Enzymatic Detection of Hybridization

In some embodiments of the present invention, hybridization is detected by enzymatic cleavage of specific structures (INVADER assay, Third Wave Technologies; See e.g., U.S. Pat. Nos. 5,846,717, 6,090,543; 6,001,567; 5,985,557; and 5,994,069; each of which is herein incorporated by reference). The INVADER assay detects specific DNA and RNA sequences by using structure-specific enzymes to cleave a complex formed by the hybridization of overlapping oligonucleotide probes. Elevated temperature and an excess of one of the probes enable multiple probes to be cleaved for each target sequence present without temperature cycling. These cleaved probes then direct cleavage of a second labeled probe. The secondary probe oligonucleotide can be 5'-end labeled with fluorescein that is quenched by an internal dye. Upon cleavage, the de-quenched fluorescein labeled product may be detected using a standard fluorescence plate reader.

The INVADER assay detects specific mutations and SNPs in unamplified genomic DNA. The isolated DNA sample is contacted with the first probe specific either for a SNP/mutation or wild type sequence and allowed to hybridize. Then a secondary probe, specific to the first probe, and containing the fluorescein label, is hybridized and the enzyme is added. Binding is detected by using a fluorescent plate reader and comparing the signal of the test sample to known positive and negative controls.

In some embodiments, hybridization of a bound probe is detected using a TaqMan assay (PE Biosystems, Foster City, Calif.; See e.g., U.S. Pat. Nos. 5,962,233 and 5,538,848, each of which is herein incorporated by reference). The assay is performed during a PCR reaction. The TaqMan assay exploits the 5'-3' exonuclease activity of the AMPLITAQ GOLD DNA polymerase. A probe, specific for a given allele or mutation, is included in the PCR reaction. The probe consists of an oligonucleotide with a 5'-reporter dye (e.g., a fluorescent dye) and a 3'-quencher dye. During PCR, if the probe is bound to its target, the 5'-3' nucleolytic activity of the AMPLITAQ GOLD polymerase cleaves the probe between the reporter and the quencher dye. The separation of the reporter dye from the quencher dye results in an increase of fluorescence. The signal accumulates with each cycle of PCR and can be monitored with a fluorimeter.

In still further embodiments, polymorphisms are detected using the SNP-IT primer extension assay (Orchid Biosciences, Princeton, N.J.; See e.g., U.S. Pat. Nos. 5,952,174 and 5,919,626, each of which is herein incorporated by reference). In this assay, SNPs are identified by using a specially synthesized DNA primer and a DNA polymerase to selectively extend the DNA chain by one base at the suspected SNP location. DNA in the region of interest is amplified and denatured. Polymerase reactions are then performed using miniaturized systems called microfluidics. Detection is accomplished by adding a label to the nucleotide suspected of being at the SNP or mutation location. Incorporation of the label into the DNA can be detected by any suitable method (e.g., if the nucleotide contains a biotin label, detection is via a fluorescently labeled antibody specific for biotin).

6. Mass Spectroscopy Assay

In some embodiments, a MassARRAY system (Sequenom, San Diego, Calif.) is used to detect variant sequences (See e.g., U.S. Pat. Nos. 6,043,031; 5,777,324; and 5,605,798; each of which is herein incorporated by reference). DNA is isolated from blood samples using standard procedures. Next, specific DNA regions containing the mutation or SNP of interest, about 200 base pairs in length, are amplified by PCR. The amplified fragments are then attached by one strand to a solid surface and the non-immobilized strands are removed by standard denaturation and washing. The remaining immobilized single strand then serves as a template for automated enzymatic reactions that produce genotype specific diagnostic products.

Very small quantities of the enzymatic products, typically five to ten nanoliters, are then transferred to a SpectroCHIP array for subsequent automated analysis with the SpectroREADER mass spectrometer. Each spot is preloaded with light absorbing crystals that form a matrix with the dispensed diagnostic product. The MassARRAY system uses MALDI-TOF (Matrix Assisted Laser Desorption Ionization—Time of Flight) mass spectrometry. In a process known as desorption, the matrix is hit with a pulse from a laser beam. Energy from the laser beam is transferred to the matrix and it is vaporized resulting in a small amount of the diagnostic product being expelled into a flight tube. As the diagnostic product is charged when an electrical field pulse is subsequently applied to the tube they are launched down the flight tube towards a detector. The time between application of the electrical field pulse and collision of the diagnostic product with the detector is referred to as the time of flight. This is a very precise measure of the product's molecular weight, as a molecule's mass correlates directly with time of flight with smaller molecules flying faster than larger molecules. The entire assay is completed in less than one thousandth of a second, enabling samples to be analyzed in a total of 3-5 second including repetitive data collection. The SpectroTYPER software then calculates, records, compares and reports the genotypes at the rate of three seconds per sample.

7. Detection of Variant SLC18A1 and TAAR2 Proteins

In other embodiments, variant (e.g., truncated or mutated) SLC18A1 polypeptides and TAAR2 polypeptides are detected (e.g., including, but not limited to, those described in SEQ ID NOs: 2 and 4). Any suitable method may be used to detect truncated or mutant SLC18A1 polypeptides or TAAR2 peptides including, but not limited to, those described below.

a) Cell Free Translation

For example, in some embodiments, cell-free translation methods from Ambergen, Inc. (Boston, Mass.) are utilized. Ambergen, Inc. has developed a method for the labeling, detection, quantitation, analysis and isolation of nascent proteins produced in a cell-free or cellular translation system without the use of radioactive amino acids or other radioactive labels. Markers are aminoacylated to tRNA molecules. Potential markers include native amino acids, non-native amino acids, amino acid analogs or derivatives, or chemical moieties. These markers are introduced into nascent proteins from the resulting misaminoacylated tRNAs during the translation process.

One application of Ambergen's protein labeling technology is the gel free truncation test (GFTT) assay (See e.g., U.S. Pat. No. 6,303,337, herein incorporated by reference). In some embodiments, this assay is used to screen for truncation mutations in SLC18A1 polypeptides and TAAR2 polypeptides. In the GFTT assay, a marker (e.g., a fluorophore) is introduced to the nascent protein during translation near the N-terminus of the protein. A second and different marker (e.g., a fluorophore with a different emission wavelength) is introduced to the nascent protein near the C-terminus of the protein. The protein is then separated from the translation system and the signal from the markers is measured. A comparison of the measurements from the N and C terminal signals provides information on the fraction of the molecules with C-terminal truncation (i.e., if the normalized signal from the C-terminal marker is 50% of the signal from the N-terminal marker, 50% of the molecules have a C-terminal truncation).

b) Antibody Binding

In still further embodiments of the present invention, antibodies (See below for antibody production) are used to determine if an individual contains an allele encoding a variant SLC18A1 or TAAR2 gene. In preferred embodiments, antibodies are utilized that discriminate between variant (i.e., truncated or mutated proteins) and wild-type proteins (SEQ ID NOs: 2 and 4). In some particularly preferred embodiments, the antibodies are directed to the C-terminus of SLC18A1 or TAAR2. In some embodiments, proteins that are recognized by the N-terminal, but not the C-terminal antibody are truncated. In some embodiments, quantitative immunoassays are used to determine the ratios of C-terminal to N-terminal antibody binding. In other embodiments, identification of variants of SLC18A1 or TAAR2 is accomplished through the use of antibodies that differentially bind to wild type or variant forms of SLC18A1 or TAAR2.

Antibody binding is detected by techniques known in the art (e.g., radioimmunoassay, ELISA (enzyme-linked immunosorbant assay), "sandwich" immunoassays, immunoradiometric assays, gel diffusion precipitation reactions, immunodiffusion assays, in situ immunoassays (e.g. using colloidal gold, enzyme or radioisotope labels, for example), Western blots, precipitation reactions, agglutination assays (e.g., gel agglutination assays, hemagglutination assays, etc.), complement fixation assays, immunofluorescence assays, protein A assays, and immunoelectrophoresis assays, etc.

In one embodiment, antibody binding is detected by detecting a label on the primary antibody. In another embodiment, the primary antibody is detected by detecting binding of a secondary antibody or reagent to the primary antibody. In a further embodiment, the secondary antibody is labeled. Many methods are known in the art for detecting binding in an immunoassay and are within the scope of the present invention.

In some embodiments, an automated detection assay is utilized. Methods for the automation of immunoassays include those described in U.S. Pat. Nos. 5,885,530, 4,981,785, 6,159,750, and 5,358,691, each of which is herein incorporated by reference. In some embodiments, the analysis and presentation of results is also automated. For example, in some embodiments, software that generates a prognosis based on the result of the immunoassay is utilized.

In other embodiments, the immunoassay described in U.S. Pat. Nos. 5,599,677 and 5,672,480; each of which is herein incorporated by reference.

8. Kits for Analyzing Risk of Neuropsychiatric Disorders

The present invention also provides kits for determining whether an individual contains a wild-type or variant (e.g., mutant or polymorphic) allele of SLC18A1 or TAAR2. In some embodiments, the kits are useful for determining whether the subject is at risk of developing neuropsychiatric disorders (e.g., schizophrenia). The diagnostic kits are produced in a variety of ways. In some embodiments, the kits contain at least one reagent for specifically detecting a mutant SLC18A1 allele or protein. In other embodiments, the kits contain at least one reagent for specifically detecting a mutant TAAR2 allele or protein. In preferred embodiments, the kits contain reagents for detecting a truncation or substitution in the SLC18A1 or TAAR2 proteins. In preferred embodiments, the reagent is a nucleic acid that hybridizes to nucleic acids containing the mutation and that does not bind to nucleic acids that do not contain the mutation. In other preferred embodiments, the reagents are primers for amplifying the region of DNA containing the mutation. In still other embodiments, the reagents are antibodies that preferentially bind either the wild-type or truncated SLC18A1 or TAAR2 proteins.

In some embodiments, the kit contains instructions for determining whether the subject is at risk for developing neuropsychiatric disorders (e.g., schizophrenia). In preferred embodiments, the instructions specify that risk for developing neuropsychiatric disorders is determined by detecting the presence or absence of a mutant SLC18A1 or TAAR2 allele in the subject, wherein subjects having a mutant (e.g., truncated or substitution) allele are at greater risk for neuropsychiatric disorders (e.g., schizophrenia).

The presence or absence of a disease-associated mutation in a SLC18A1 or TAAR2 gene can be used to make therapeutic or other medical decisions. For example, couples with a family history of schizophrenia may choose to conceive a child via in vitro fertilization and pre-implantation genetic screening. In this case, fertilized embryos are screened for mutant (e.g., disease associated) alleles of the SLC18A1 or TAAR2 gene and only embryos with wild type alleles are implanted in the uterus.

In other embodiments, in utero screening is performed on a developing fetus (e.g., amniocentesis or chorionic villi screening). In still other embodiments, genetic screening of newborn babies or very young children is performed. The early detection of a SLC18A1 or TAAR2 allele known to be associated with neuropsychiatric disorders allows for early intervention (e.g., genetic or pharmaceutical therapies).

In some embodiments, the kits include ancillary reagents such as buffering agents, nucleic acid stabilizing reagents, protein stabilizing reagents, and signal producing systems (e.g., florescence generating systems as Fret systems). The test kit may be packages in any suitable manner, typically with the elements in a single container or various containers as necessary along with a sheet of instructions for carrying out the test. In some embodiments, the kits also preferably include a positive control sample.

9. Bioinformatics

In some embodiments, the present invention provides methods of determining an individual's risk of developing neuropsychiatric disease based on the presence of one or more variant alleles of SLC18A1 or TAAR2. In some embodiments, the analysis of variant data is processed by a computer using information stored on a computer (e.g., in a database). For example, in some embodiments, the present invention provides a bioinformatics research system comprising a plurality of computers running a multi-platform object oriented programming language (See e.g., U.S. Pat. No. 6,125,383; herein incorporated by reference). In some embodiments, one of the computers stores genetics data (e.g., the risk of neuropsychiatric disorders associated with a given polymorphism, as well as the sequences). In some embodiments, one of the computers stores application programs (e.g., for analyzing the results of detection assays). Results are then delivered to the user (e.g., via one of the computers or via the internet).

For example, in some embodiments, a computer-based analysis program is used to translate the raw data generated by the detection assay (e.g., the presence, absence, or amount of a given SLC18A1 allele or polypeptide) into data of predictive value for a clinician. The clinician can access the predictive data using any suitable means. Thus, in some preferred embodiments, the present invention provides the further benefit that the clinician, who is not likely to be trained in genetics or molecular biology, need not understand the raw data. The data is presented directly to the clinician in its most useful form. The clinician is then able to immediately utilize the information in order to optimize the care of the subject.

The present invention contemplates any method capable of receiving, processing, and transmitting the information to and from laboratories conducting the assays, information provides, medical personal, and subjects. For example, in some embodiments of the present invention, a sample (e.g., a biopsy or a serum or urine sample) is obtained from a subject and submitted to a profiling service (e.g., clinical lab at a medical facility, genomic profiling business, etc.), located in any part of the world (e.g., in a country different than the country where the subject resides or where the information is ultimately used) to generate raw data. Where the sample comprises a tissue or other biological sample, the subject may visit a medical center to have the sample obtained and sent to the profiling center, or subjects may collect the sample themselves (e.g., a urine sample) and directly send it to a profiling center. Where the sample comprises previously determined biological information, the information may be directly sent to the profiling service by the subject (e.g., an information card containing the information may be scanned by a computer and the data transmitted to a computer of the profiling center using an electronic communication systems). Once received by the profiling service, the sample is processed and a profile is produced (i.e., presence of wild type or mutant SLC18A1 or TAAR2 genes or polypeptides), specific for the diagnostic or prognostic information desired for the subject.

The profile data is then prepared in a format suitable for interpretation by a treating clinician. For example, rather than providing raw data, the prepared format may represent a diagnosis or risk assessment (e.g., likelihood of developing neuropsychiatric disorders or a diagnosis of a neuropsychiatric disorder such as schizophrenia) for the subject, along with recommendations for particular treatment options. The data may be displayed to the clinician by any suitable method. For example, in some embodiments, the profiling service generates a report that can be printed for the clinician (e.g., at the point of care) or displayed to the clinician on a computer monitor.

In some embodiments, the information is first analyzed at the point of care or at a regional facility. The raw data is then sent to a central processing facility for further analysis and/or to convert the raw data to information useful for a clinician or patient. The central processing facility provides the advantage of privacy (all data is stored in a central facility with uniform security protocols), speed, and uniformity of data analysis. The central processing facility can then control the fate of the data following treatment of the subject. For example, using an electronic communication system, the central facility can provide data to the clinician, the subject, or researchers.

In some embodiments, the subject is able to directly access the data using the electronic communication system. The subject may chose further intervention or counseling based on the results. In some embodiments, the data is used for research use. For example, the data may be used to further optimize the inclusion or elimination of markers as useful indicators of a particular condition or stage of disease.

II. Generation of SLC18A1 and TAAR2 Antibodies

The present invention provides isolated antibodies or antibody fragments (e.g., FAB fragments). Antibodies can be generated to allow for the detection of SLC18A1 protein or TAAR2 protein, with or without the diagnostic marker (i.e., mutation) of the present invention. The antibodies may be prepared using various immunogens. In one embodiment, the immunogen is a human SLC18A1 peptide or TAAR2 peptide to generate antibodies that recognize human SLC18A1 or TAAR2, respectively. Such antibodies include, but are not limited to polyclonal, monoclonal, chimeric, single chain, Fab fragments, Fab expression libraries, or recombinant (e.g., chimeric, humanized, etc.) antibodies, as long as it can recognize the protein. Antibodies can be produced by using a protein of the present invention as the antigen according to a conventional antibody or antiserum preparation process.

Various procedures known in the art may be used for the production of polyclonal antibodies directed against SLC18A1 or TAAR2. For example, for the production of antibody, various host animals can be immunized by injection with the peptide corresponding to the SLC18A1 epitope including but not limited to rabbits, mice, rats, sheep, goats, etc. In a preferred embodiment, the peptide is conjugated to an immunogenic carrier (e.g., diphtheria toxoid, bovine serum albumin (BSA), or keyhole limpet hemocyanin (KLH)). Various adjuvants may be used to increase the immunological response, depending on the host species, including but not limited to Freund's (complete and incomplete), mineral gels (e.g., aluminum hydroxide), surface active substances (e.g., lysolecithin, pluronic polyols, polyanions, peptides, oil emulsions, keyhole limpet hemocyanins, dinitrophenol, and potentially useful human adjuvants such as BCG (Bacille Calmette-Guerin) and *Corynebacterium parvum*).

For preparation of monoclonal antibodies directed toward SLC18A1 or TAAR2, it is contemplated that any technique that provides for the production of antibody molecules by continuous cell lines in culture will find use with the present invention (See e.g., Harlow and Lane, *Antibodies: A Laboratory Manual*, Cold Spring Harbor Laboratory Press, Cold Spring Harbor, N.Y.). These include but are not limited to the hybridoma technique originally developed by Köhler and Milstein (Köhler and Milstein, Nature 256:495-497 (1975)), as well as the trioma technique, the human B-cell hybridoma technique (See e.g., Kozbor et al., Immunol. Tod., 4:72 (1983)), and the EBV-hybridoma technique to produce human monoclonal antibodies (Cole et al., in *Monoclonal Antibodies and Cancer Therapy*, Alan R. Liss, Inc., pp. 77-96 (1985)).

In an additional embodiment of the invention, monoclonal antibodies are produced in germ-free animals utilizing technology such as that described in PCT/US90/02545). Furthermore, it is contemplated that human antibodies will be generated by human hybridomas (Cote et al., Proc. Natl. Acad. Sci. USA 80:2026-2030 (1983)) or by transforming human B cells with EBV virus in vitro (Cole et al., in *Monoclonal Antibodies and Cancer Therapy*, Alan R. Liss, pp. 77-96 (1985)).

In addition, it is contemplated that techniques described for the production of single chain antibodies (U.S. Pat. No. 4,946,778; herein incorporated by reference) will find use in producing SLC18A1 specific single chain antibodies. An additional embodiment of the invention utilizes the techniques described for the construction of Fab expression libraries (Huse et al., Science 246:1275-1281 (1989)) to allow rapid and easy identification of monoclonal Fab fragments with the desired specificity for SLC18A1.

In other embodiments, the present invention contemplated recombinant antibodies or fragments thereof to the proteins of the present invention. Recombinant antibodies include, but are not limited to, humanized and chimeric antibodies. Methods for generating recombinant antibodies are known in the art (See e.g., U.S. Pat. Nos. 6,180,370 and 6,277,969 and "Monoclonal Antibodies" H. Zola, BIOS Scientific Publishers Limited 2000. Springer-Verlay New York, Inc., New York; each of which is herein incorporated by reference).

It is contemplated that any technique suitable for producing antibody fragments will find use in generating antibody fragments that contain the idiotype (antigen binding region) of the antibody molecule. For example, such fragments include but are not limited to: F(ab')2 fragment that can be produced by pepsin digestion of the antibody molecule; Fab' fragments that can be generated by reducing the disulfide bridges of the F(ab')2 fragment, and Fab fragments that can be generated by treating the antibody molecule with papain and a reducing agent.

In the production of antibodies, it is contemplated that screening for the desired antibody will be accomplished by techniques known in the art (e.g., radioimmunoassay, ELISA (enzyme-linked immunosorbant assay), "sandwich" immunoassays, immunoradiometric assays, gel diffusion precipitation reactions, immunodiffusion assays, in situ immunoassays (e.g., using colloidal gold, enzyme or radioisotope labels, for example), Western blots, precipitation reactions, agglutination assays (e.g., gel agglutination assays, hemagglutination assays, etc.), complement fixation assays, immunofluorescence assays, protein A assays, and immunoelectrophoresis assays, etc.

In one embodiment, antibody binding is detected by detecting a label on the primary antibody. In another embodiment, the primary antibody is detected by detecting binding of a secondary antibody or reagent to the primary antibody. In a further embodiment, the secondary antibody is labeled. Many means are known in the art for detecting binding in an immunoassay and are within the scope of the present invention. As is well known in the art, the immunogenic peptide should be provided free of the carrier molecule used in any immunization protocol. For example, if the peptide was conjugated to KLH, it may be conjugated to BSA, or used directly, in a screening assay.)

Additionally, using the above methods, antibodies can be generated that recognize the variant forms of SLC18A1 or TAAR2, while not recognizing the wild type forms of the SLC18A1 or TAAR2 proteins.

The foregoing antibodies can be used in methods known in the art relating to the localization and structure of SLC18A1 and TAAR2 (e.g., for Western blotting, immunoprecipitaion and immunocytochemistry), measuring levels thereof in appropriate biological samples, etc. The antibodies can be used to detect SLC18A1 or TAAR2 in a biological sample from an individual. The biological sample can be a biological fluid, such as, but not limited to, blood, serum, plasma, interstitial fluid, urine, cerebrospinal fluid, and the like, containing cells.

The biological samples can then be tested directly for the presence of human SLC18A1 using an appropriate strategy (e.g., ELISA or radioimmunoassay) and format (e.g., microwells, dipstick (e.g., as described in International Patent Publication WO 93/03367), etc. Alternatively, proteins in the sample can be size separated (e.g., by polyacrylamide gel electrophoresis (PAGE), in the presence or not of sodium dodecyl sulfate (SDS), and the presence of SLC18A1 detected by immunoblotting (Western blotting). Immunoblotting techniques are generally more effective with antibodies generated against a peptide corresponding to an epitope of a protein, and hence, are particularly suited to the present invention.

Another method uses antibodies as agents to alter signal transduction. Specific antibodies that bind to the binding domains of SLC18A1 or TAAR2 or other proteins involved in intracellular signaling can be used to inhibit the interaction between the various proteins and their interaction with other ligands. Antibodies that bind to the complex can also be used therapeutically to inhibit interactions of the protein complex in the signal transduction pathways leading to the various physiological and cellular effects of SLC18A1 or TAAR2. Such antibodies can also be used diagnostically to measure abnormal expression of SLC18A1 or TAAR2, or the aberrant formation of protein complexes, which may be indicative of a disease state.

III. Gene Therapy Using SLC18A1 and TAAR2

The present invention also provides methods and compositions suitable for gene therapy to alter SLC18A1 or TAAR2 expression, production, or function. As described above, the present invention provides human SLC18A1 genes and TAAR2 genes and provides methods of obtaining SLC18A1 genes or TAAR2 genes from other species. Thus, the methods described below are generally applicable across many species. In some embodiments, it is contemplated that the gene therapy is performed by providing a subject with a wild-type allele of SLC18A1 or TAAR2 (i.e., an allele that does not contain a neuropsychiatric disease causing polymorphisms or mutations). Subjects in need of such therapy are identified by the methods described above.

Viral vectors commonly used for in vivo or ex vivo targeting and therapy procedures are DNA-based vectors and retroviral vectors. Methods for constructing and using viral vectors are known in the art (See e.g., Miller and Rosman, BioTech., 7:980-990 (1992)). Preferably, the viral vectors are replication defective, that is, they are unable to replicate autonomously in the target cell. In general, the genome of the replication defective viral vectors that are used within the scope of the present invention lack at least one region that is necessary for the replication of the virus in the infected cell. These regions can either be eliminated (in whole or in part), or be rendered non-functional by any technique known to a person skilled in the art. These techniques include the total removal, substitution (by other sequences, in particular by the inserted nucleic acid), partial deletion or addition of one or more bases to an essential (for replication) region. Such techniques may be performed in vitro (i.e., on the isolated DNA) or in situ, using the techniques of genetic manipulation or by treatment with mutagenic agents.

Preferably, the replication defective virus retains the sequences of its genome that are necessary for encapsidating the viral particles. DNA viral vectors include an attenuated or defective DNA viruses, including, but not limited to, herpes simplex virus (HSV), papillomavirus, Epstein Barr virus (EBV), adenovirus, adeno-associated virus (AAV), and the like. Defective viruses, that entirely or almost entirely lack viral genes, are preferred, as defective virus is not infective after introduction into a cell. Use of defective viral vectors allows for administration to cells in a specific, localized area, without concern that the vector can infect other cells. Thus, a specific tissue can be specifically targeted. Examples of particular vectors include, but are not limited to, a defective herpes virus 1 (HSV1) vector (Kaplitt et al., Mol. Cell. Neurosci., 2:320-330 (1991)), defective herpes virus vector lacking a glycoprotein L gene (See e.g., Patent Publication RD 371005 A), or other defective herpes virus vectors (See e.g., WO 94/21807; and WO 92/05263); an attenuated adenovirus vector, such as the vector described by Stratford-Perricaudet et al. (J. Clin. Invest., 90:626-630 (1992); See also, La Salle et al., Science 259:988-990 (1993)); and a defective adeno-associated virus vector (Samulski et al., J. Virol., 61:3096-3101 (1987); Samulski et al., J. Virol., 63:3822-3828 (1989); and Lebkowski et al., Mol. Cell. Biol., 8:3988-3996 (1988)).

Preferably, for in vivo administration, an appropriate immunosuppressive treatment is employed in conjunction with the viral vector (e.g., adenovirus vector), to avoid immuno-deactivation of the viral vector and transfected cells. For example, immunosuppressive cytokines, such as interleukin-12 (IL-12), interferon-gamma (IFN-γ), or anti-CD4 antibody, can be administered to block humoral or cellular immune responses to the viral vectors. In addition, it is advantageous to employ a viral vector that is engineered to express a minimal number of antigens.

In a preferred embodiment, the vector is an adenovirus vector. Adenoviruses are eukaryotic DNA viruses that can be modified to efficiently deliver a nucleic acid of the invention to a variety of cell types. Various serotypes of adenovirus exist. Of these serotypes, preference is given, within the scope of the present invention, to type 2 or type 5 human adenoviruses (Ad 2 or Ad 5), or adenoviruses of animal origin (See e.g., WO 94/26914). Those adenoviruses of animal origin that can be used within the scope of the present invention include adenoviruses of canine, bovine, murine (e.g., Mav1, Beard et al., Virol., 75-81 (1990)), ovine, porcine, avian, and simian (e.g., SAV) origin. Preferably, the adenovirus of animal origin is a canine adenovirus, more preferably a CAV2 adenovirus (e.g. Manhattan or A26/61 strain (ATCC VR-800)).

Preferably, the replication defective adenoviral vectors of the invention comprise the ITRs, an encapsidation sequence and the nucleic acid of interest. Still more preferably, at least the E1 region of the adenoviral vector is non-functional. The deletion in the E1 region preferably extends from nucleotides 455 to 3329 in the sequence of the Ad5 adenovirus (PvuII-BglII fragment) or 382 to 3446 (HinfII-Sau3A fragment). Other regions may also be modified, in particular the E3 region (e.g., WO 95/02697), the E2 region (e.g., WO 94/28938), the E4 region (e.g., WO 94/28152, WO 94/12649 and WO 95/02697), or in any of the late genes L1-L5.

In a preferred embodiment, the adenoviral vector has a deletion in the E1 region (Ad 1.0). Examples of E1-deleted adenoviruses are disclosed in EP 185,573, the contents of which are incorporated herein by reference. In another preferred embodiment, the adenoviral vector has a deletion in the E1 and E4 regions (Ad 3.0). Examples of E1/E4-deleted adenoviruses are disclosed in WO 95/02697 and WO 96/22378. In still another preferred embodiment, the adenoviral vector has a deletion in the E1 region into which the E4 region and the nucleic acid sequence are inserted.

The replication defective recombinant adenoviruses according to the invention can be prepared by any technique known to the person skilled in the art (See e.g., Levrero et al., Gene 101:195 (1991); EP 185573; and Graham, EMBO J., 3:2917 (1984)). In particular, they can be prepared by homologous recombination between an adenovirus and a plasmid that carries, inter alia, the DNA sequence of interest. The homologous recombination is accomplished following co-transfection of the adenovirus and plasmid into an appropriate cell line. The cell line that is employed should preferably (i) be transformable by the elements to be used, and (ii) contain the sequences that are able to complement the part of the genome of the replication defective adenovirus, preferably in integrated form in order to avoid the risks of recombination. Examples of cell lines that may be used are the human embryonic kidney cell line 293 (Graham et al., J. Gen. Virol., 36:59 (1977)), which contains the left-hand portion of the genome of an Ad5 adenovirus (12%) integrated into its genome, and cell lines that are able to complement the E1 and E4 functions, as described in applications WO 94/26914 and WO 95/02697. Recombinant adenoviruses are recovered and purified using standard molecular biological techniques that are well known to one of ordinary skill in the art.

The adeno-associated viruses (AAV) are DNA viruses of relatively small size that can integrate, in a stable and site-specific manner, into the genome of the cells that they infect. They are able to infect a wide spectrum of cells without inducing any effects on cellular growth, morphology or differentiation, and they do not appear to be involved in human pathologies. The AAV genome has been cloned, sequenced and characterized. It encompasses approximately 4700 bases and contains an inverted terminal repeat (ITR) region of approximately 145 bases at each end, which serves as an origin of replication for the virus. The remainder of the genome is divided into two essential regions that carry the encapsidation functions: the left-hand part of the genome, that contains the rep gene involved in viral replication and expression of the viral genes; and the right-hand part of the genome, that contains the cap gene encoding the capsid proteins of the virus.

The use of vectors derived from the AAVs for transferring genes in vitro and in vivo has been described (See e.g., WO 91/18088; WO 93/09239; U.S. Pat. No. 4,797,368; U.S. Pat. No. 5,139,941; and EP 488 528, all of which are herein incorporated by reference). These publications describe various AAV-derived constructs in which the rep and/or cap genes are deleted and replaced by a gene of interest, and the use of these constructs for transferring the gene of interest in vitro (into cultured cells) or in vivo (directly into an organism). The replication defective recombinant AAVs according to the invention can be prepared by co-transfecting a plasmid containing the nucleic acid sequence of interest flanked by two AAV inverted terminal repeat (ITR) regions, and a plasmid carrying the AAV encapsidation genes (rep and cap genes), into a cell line that is infected with a human helper virus (for example an adenovirus). The AAV recombinants that are produced are then purified by standard techniques.

In another embodiment, the gene can be introduced in a retroviral vector (e.g., as described in U.S. Pat. Nos. 5,399, 346, 4,650,764, 4,980,289 and 5,124,263; all of which are herein incorporated by reference; Mann et al., Cell 33:153 (1983); Markowitz et al., J. Virol., 62:1120 (1988); PCT/US95/14575; EP 453242; EP178220; Bernstein et al. Genet. Eng., 7:235 (1985); McCormick, BioTechnol., 3:689 (1985); WO 95/07358; and Kuo et al., Blood 82:845 (1993)). The retroviruses are integrating viruses that infect dividing cells. The retrovirus genome includes two LTRs, an encapsidation sequence and three coding regions (gag, pol and env). In recombinant retroviral vectors, the gag, pol and env genes are generally deleted, in whole or in part, and replaced with a heterologous nucleic acid sequence of interest. These vectors can be constructed from different types of retrovirus, such as, HIV, MoMuLV ("murine Moloney leukemia virus" MSV ("murine Moloney sarcoma virus"), HaSV ("Harvey sarcoma virus"); SNV ("spleen necrosis virus"); RSV ("Rous sarcoma virus") and Friend virus. Defective retroviral vectors are also disclosed in WO 95/02697.

In general, in order to construct recombinant retroviruses containing a nucleic acid sequence, a plasmid is constructed that contains the LTRs, the encapsidation sequence and the coding sequence. This construct is used to transfect a packaging cell line, which cell line is able to supply in trans the retroviral functions that are deficient in the plasmid. In general, the packaging cell lines are thus able to express the gag, pol and env genes. Such packaging cell lines have been described in the prior art, in particular the cell line PA317 (U.S. Pat. No. 4,861,719, herein incorporated by reference), the PsiCRIP cell line (See, WO90/02806), and the GP+en-vAm-12 cell line (See, WO89/07150). In addition, the recombinant retroviral vectors can contain modifications within the LTRs for suppressing transcriptional activity as well as extensive encapsidation sequences that may include a part of the gag gene (Bender et al., J. Virol., 61:1639 (1987)). Recombinant retroviral vectors are purified by standard techniques known to those having ordinary skill in the art.

Alternatively, the vector can be introduced in vivo by lipofection. For the past decade, there has been increasing use of liposomes for encapsulation and transfection of nucleic acids in vitro. Synthetic cationic lipids designed to limit the difficulties and dangers encountered with liposome mediated transfection can be used to prepare liposomes for in vivo transfection of a gene encoding a marker (Felgner et. al., Proc. Natl. Acad. Sci. USA 84:7413-7417 (1987); See also, Mackey, et al., Proc. Natl. Acad. Sci. USA 85:8027-8031 (1988); Ulmer et al., Science 259:1745-1748 (1993)). The use of cationic lipids may promote encapsulation of negatively charged nucleic acids, and also promote fusion with negatively charged cell membranes (Felgner and Ringold, Science 337:387-388 (1989)). Particularly useful lipid compounds and compositions for transfer of nucleic acids are described in WO95/18863 and WO96/17823, and in U.S. Pat. No. 5,459, 127, herein incorporated by reference.

Other molecules are also useful for facilitating transfection of a nucleic acid in vivo, such as a cationic oligopeptide (e.g., WO95/21931), peptides derived from DNA binding proteins (e.g., WO96/25508), or a cationic polymer (e.g., WO95/21931).

It is also possible to introduce the vector in vivo as a naked DNA plasmid. Methods for formulating and administering naked DNA to mammalian muscle tissue are disclosed in U.S. Pat. Nos. 5,580,859 and 5,589,466, both of which are herein incorporated by reference.

DNA vectors for gene therapy can be introduced into the desired host cells by methods known in the art, including but not limited to transfection, electroporation, microinjection, transduction, cell fusion, DEAE dextran, calcium phosphate precipitation, use of a gene gun, or use of a DNA vector transporter (See e.g., Wu et al., J. Biol. Chem., 267:963 (1992); Wu and Wu, J. Biol. Chem., 263:14621 (1988); and Williams et al., Proc. Natl. Acad. Sci. USA 88:2726 (1991)). Receptor-mediated DNA delivery approaches can also be used (Curiel et al., Hum. Gene Ther., 3:147 (1992); and Wu and Wu, J. Biol. Chem., 262:4429 (1987)).

IV. Transgenic Animals Expressing Exogenous SLC18A1 or TAAR2 Genes and Homologs, Mutants, and Variants Thereof The present invention contemplates the generation of transgenic animals comprising an exogenous SLC18A1 gene or TAAR2 gene or homologs, mutants, or variants thereof. In preferred embodiments, the transgenic animal displays an altered phenotype as compared to wild-type animals. In some embodiments, the altered phenotype is the overexpression (e.g., wild type or mutant, See Examples 1 and 2) mRNA for a SLC18A1 gene or TAAR2 gene as compared to wild-type levels of SLC18A1 or TAAR2 expression. In other embodiments, the altered phenotype is the decreased expression of mRNA for an endogenous SLC18A1 gene or TAAR2 gene as compared to wild-type levels of endogenous SLC18A1 or TAAR2 expression. In some preferred embodiments, the transgenic animals comprise mutant (e.g., truncated) alleles of SLC18A1 or TAAR2. Methods for analyzing the presence or absence of such phenotypes include Northern blotting, mRNA protection assays, and RT-PCR. In other embodiments, the transgenic mice have a knock out mutation of the SLC18A1 gene or TAAR2 gene. In preferred embodiments, the transgenic animals display a neuropsychiatric disorder phenotype.

Such animals find use in research applications (e.g., identifying signaling pathways involved in neuropsychiatric disorders), as well as drug screening applications (e.g., to screen for drugs that prevents neuropsychiatric disorder/disease). For example, in some embodiments, test compounds (e.g., a drug that is suspected of being useful to treat neuropsychiatric disorders) and control compounds (e.g., a placebo) are administered to the transgenic animals and the control animals and the effects evaluated. The effects of the test and control compounds on disease symptoms are then assessed.

The transgenic animals can be generated via a variety of methods. In some embodiments, embryonal cells at various developmental stages are used to introduce transgenes for the production of transgenic animals. Different methods are used depending on the stage of development of the embryonal cell. The zygote is the best target for micro-injection. In the mouse, the male pronucleus reaches the size of approximately 20 micrometers in diameter, which allows reproducible injection of 1-2 picoliters (pl) of DNA solution. The use of zygotes as a target for gene transfer has a major advantage in that in most cases the injected DNA will be incorporated into the host genome before the first cleavage (Brinster et al., Proc. Natl. Acad. Sci. USA 82:4438-4442 (1985)). As a consequence, all cells of the transgenic non-human animal will carry the incorporated transgene. This will in general also be reflected in the efficient transmission of the transgene to offspring of the founder since 50% of the germ cells will harbor the transgene. U.S. Pat. No. 4,873,191 describes a method for the micro-injection of zygotes; the disclosure of this patent is incorporated herein in its entirety.

In other embodiments, retroviral infection is used to introduce transgenes into a non-human animal. In some embodiments, the retroviral vector is utilized to transfect oocytes by injecting the retroviral vector into the perivitelline space of the oocyte (U.S. Pat. No. 6,080,912, incorporated herein by reference). In other embodiments, the developing non-human embryo can be cultured in vitro to the blastocyst stage. During this time, the blastomeres can be targets for retroviral infection (Janenich, Proc. Natl. Acad. Sci. USA 73:1260 (1976)). Efficient infection of the blastomeres is obtained by enzymatic treatment to remove the zona pellucida (Hogan et al., in *Manipulating the Mouse Embryo*, Cold Spring Harbor Laboratory Press, Cold Spring Harbor, N.Y. (1986)). The viral vector system used to introduce the transgene is typically a replication-defective retrovirus carrying the transgene (Jahner et al., Proc. Natl. Acad. Sci. USA 82:6927 (1985)). Transfection is easily and efficiently obtained by culturing the blastomeres on a monolayer of virus-producing cells (Van der Putten, supra; Stewart, et al., EMBO J., 6:383 (1987)). Alternatively, infection can be performed at a later stage. Virus or virus-producing cells can be injected into the blastocoele (Jahner et al., Nature 298:623 (1982)). Most of the founders will be mosaic for the transgene since incorporation occurs only in a subset of cells that form the transgenic animal. Further, the founder may contain various retroviral insertions of the transgene at different positions in the genome that generally will segregate in the offspring. In addition, it is also possible to introduce transgenes into the germline, albeit with low efficiency, by intrauterine retroviral infection of the midgestation embryo (Jahner et al., supra (1982)). Additional means of using retroviruses or retroviral vectors to create transgenic animals known to the art involves the micro-injection of retroviral particles or mitomycin C-treated cells producing retrovirus into the perivitelline space of fertilized eggs or early embryos (PCT International Application WO 90/08832 (1990), and Haskell and Bowen, Mol. Reprod. Dev., 40:386 (1995)).

In other embodiments, the transgene is introduced into embryonic stem cells and the transfected stem cells are utilized to form an embryo. ES cells are obtained by culturing pre-implantation embryos in vitro under appropriate conditions (Evans et al., Nature 292:154 (1981); Bradley et al., Nature 309:255 (1984); Gossler et al., Proc. Acad. Sci. USA 83:9065 (1986); and Robertson et al., Nature 322:445 (1986)). Transgenes can be efficiently introduced into the ES cells by DNA transfection by a variety of methods known to the art including calcium phosphate co-precipitation, protoplast or spheroplast fusion, lipofection and DEAE-dextran-mediated transfection. Transgenes may also be introduced into ES cells by retrovirus-mediated transduction or by micro-injection. Such transfected ES cells can thereafter colonize an embryo following their introduction into the blastocoel of a blastocyst-stage embryo and contribute to the germ line of the resulting chimeric animal (for review, See, Jaenisch, Science 240:1468 (1988)). Prior to the introduction of transfected ES cells into the blastocoel, the transfected ES cells may be subjected to various selection protocols to enrich for ES cells which have integrated the transgene assuming that the transgene provides a means for such selection. Alternatively, the polymerase chain reaction may be used to screen for ES cells that have integrated the transgene. This technique obviates the need for growth of the transfected ES cells under appropriate selective conditions prior to transfer into the blastocoel.

In still other embodiments, homologous recombination is utilized to knock-out gene function or create deletion mutants (e.g., mutants in which the LRRs of SLC18A1 are deleted). Methods for homologous recombination are described in U.S. Pat. No. 5,614,396, incorporated herein by reference.

V. Drug Screening Using SLC18A1 and TAAR2

As described herein, it is contemplated that SCL18A1 and TAAR2 interact within a novel shared pathogenic pathway. Accordingly, in some embodiments, the isolated nucleic acid sequences of SLC18A1 (e.g., SEQ ID NOS: 1 and 2) and TAAR2 (e.g., SEQ ID NOS.: 3 and 4) are used in drug screening applications for compounds that alter (e.g., enhance) signaling within the pathway.

A. Identification of Binding Partners

In some embodiments, binding partners of SLC18A1 amino acids and TAAR2 amino acids are identified. In some embodiments, the SLC18A1 nucleic acid sequence and TAAR2 nucleic acid sequences or fragments thereof are used in yeast two-hybrid screening assays. For example, in some embodiments, the nucleic acid sequences are subcloned into pGPT9 (Clontech, La Jolla, Calif.) to be used as a bait in a yeast-2-hybrid screen for protein-protein interaction of a human brain cDNA library (Fields and Song *Nature* 340:245-246, 1989; herein incorporated by reference). In other embodiments, phage display is used to identify binding partners (Parmley and Smith *Gene* 73: 305-318, (1988); herein incorporated by reference).

B. Drug Screening

The present invention provides methods and compositions for using SLC18A1 and TAAR2 as a target for screening drugs that can alter, for example, interaction between SLC18A1 and TAAR2 and their binding partners (e.g., those identified using the above methods)

In one screening method, the two-hybrid system is used to screen for compounds (e.g., drug) capable of altering (e.g., inhibiting) SLC18A1 function(s) or TAAR2 function(s) (e.g., interaction with a binding partner) in vitro or in vivo. In one embodiment, a GAL4 binding site, linked to a reporter gene such as lacZ, is contacted in the presence and absence of a candidate compound with a GAL4 binding domain linked to a SLC18A1 fragment or a TAAR2 fragment and a GAL4 transactivation domain II linked to a binding partner fragment. Expression of the reporter gene is monitored and a decrease in the expression is an indication that the candidate compound inhibits the interaction of SLC18A1 or TAAR2 with the binding partner. Alternately, the effect of candidate compounds on the interaction of SLC18A1 with other proteins (e.g., proteins known to interact directly or indirectly with the binding partner) can be tested in a similar manner.

In another screening method, candidate compounds are evaluated for their ability to alter SLC18A1 signaling or TAAR2 signaling by contacting SLC18A1 or TAAR2, binding partners, binding partner-associated proteins, or fragments thereof, with the candidate compound and determining binding of the candidate compound to the peptide. The protein or protein fragments is/are immobilized using methods known in the art such as binding a GST-SLC18A1 or a GST-TAAR2 fusion protein to a polymeric bead containing glutathione. A chimeric gene encoding a GST fusion protein is constructed by fusing DNA encoding the polypeptide or polypeptide fragment of interest to the DNA encoding the carboxyl terminus of GST (See e.g., Smith et al., Gene 67:31 (1988)). The fusion construct is then transformed into a suitable expression system (e.g., *E. coli* XA90) in which the expression of the GST fusion protein can be induced with isopropyl-β-D-thiogalactopyranoside (IPTG). Induction with IPTG should yield the fusion protein as a major constituent of soluble, cellular proteins. The fusion proteins can be purified by methods known to those skilled in the art, including purification by glutathione affinity chromatography. Binding of the candidate compound to the proteins or protein fragments is correlated with the ability of the compound to disrupt the signal transduction pathway and thus regulate SLC18A1 or TAAR2 physiological effects (e.g., neuropsychiatric disease).

In another screening method, one of the components of the SLC18A1 or TAAR2/binding partner signaling system, is immobilized. Polypeptides can be immobilized using methods known in the art, such as adsorption onto a plastic microtiter plate or specific binding of a GST-fusion protein to a polymeric bead containing glutathione. For example, GST-SLC18A1 or GST-TAAR2 is bound to glutathione-Sepharose beads. The immobilized peptide is then contacted with another peptide with which it is capable of binding in the presence and absence of a candidate compound. Unbound peptide is then removed and the complex solubilized and analyzed to determine the amount of bound labeled peptide. A decrease in binding is an indication that the candidate compound inhibits the interaction of SLC18A1 or TAAR2 with the other peptide. A variation of this method allows for the screening of compounds that are capable of disrupting a previously-formed protein/protein complex. For example, in some embodiments a complex comprising SLC18A1 or TAAR2 or fragments thereof bound to another peptide is immobilized as described above and contacted with a candidate compound. The dissolution of the complex by the candidate compound correlates with the ability of the compound to disrupt or inhibit the interaction between SLC18A1 or TAAR2 and the other peptide.

Another technique for drug screening provides high throughput screening for compounds having suitable binding affinity to SLC18A1 peptides or TAAR2 peptides and is described in detail in WO 84/03564, incorporated herein by reference. Briefly, large numbers of different small peptide test compounds are synthesized on a solid substrate, such as plastic pins or some other surface. The peptide test compounds are then reacted with SLC18A1 peptides or TAAR2 peptides and washed. Bound SLC18A1 peptides or TAAR2 peptides are then detected by methods well known in the art.

Another technique uses SLC18A1 antibodies or TAAR2 antibodies, generated as discussed above. Such antibodies capable of specifically binding to SLC18A1 peptides or TAAR2 peptides compete with a test compound for binding to SLC18A1 or TAAR2. In this manner, the antibodies can be used to detect the presence of any peptide that shares one or more antigenic determinants of the SLC18A1 peptide or TAAR2 peptide.

The present invention contemplates many other means of screening compounds. The examples provided above are presented merely to illustrate a range of techniques available. One of ordinary skill in the art will appreciate that many other screening methods can be used.

In particular, the present invention contemplates the use of cell lines transfected with SLC18A1 and TAAR2 and variants thereof for screening compounds for activity, and in particular to high throughput screening of compounds from combinatorial libraries (e.g., libraries containing greater than $10^4$ compounds). The cell lines of the present invention can be used in a variety of screening methods. In some embodiments, the cells can be used in second messenger assays that monitor signal transduction following activation of cell-surface receptors. In other embodiments, the cells can be used in reporter gene assays that monitor cellular responses at the transcription/translation level. In still further embodiments, the cells can be used in cell proliferation assays to monitor the overall growth/no growth response of cells to external stimuli.

In second messenger assays, the host cells are preferably transfected as described above with vectors encoding SLC18A1 or TAAR2 or variants or mutants thereof. The host cells are then treated with a compound or plurality of compounds (e.g., from a combinatorial library) and assayed for the presence or absence of a response. It is contemplated that at least some of the compounds in the combinatorial library can serve as agonists, antagonists, activators, or inhibitors of the protein or proteins encoded by the vectors. It is also contemplated that at least some of the compounds in the combinatorial library can serve as agonists, antagonists, activators, or inhibitors of protein acting upstream or downstream of the protein encoded by the vector in a signal transduction pathway.

In some embodiments, the second messenger assays measure fluorescent signals from reporter molecules that respond to intracellular changes (e.g., $Ca^{2+}$ concentration, membrane potential, pH, $IP_3$, cAMP, arachidonic acid release) due to stimulation of membrane receptors and ion channels (e.g., ligand gated ion channels; see Denyer et al., Drug Discov. Today 3:323 (1998); and Gonzales et al., Drug. Discov. Today 4:431-39 (1999)). Examples of reporter molecules include, but are not limited to, FRET (florescence resonance energy transfer) systems (e.g., Cuo-lipids and oxonols, EDAN/DAB-CYL), calcium sensitive indicators (e.g., Fluo-3, FURA 2, INDO 1, and FLUO3/AM, BAPTA AM), chloride-sensitive indicators (e.g., SPQ, SPA), potassium-sensitive indicators (e.g., PBFI), sodium-sensitive indicators (e.g., SBFI), and pH sensitive indicators (e.g., BCECF).

In general, the host cells are loaded with the indicator prior to exposure to the compound. Responses of the host cells to treatment with the compounds can be detected by methods known in the art, including, but not limited to, fluorescence microscopy, confocal microscopy (e.g., FCS systems), flow cytometry, microfluidic devices, FLIPR systems (See, e.g., Schroeder and Neagle, J. Biomol. Screening 1:75 (1996)), and plate-reading systems. In some preferred embodiments, the response (e.g., increase in fluorescent intensity) caused by compound of unknown activity is compared to the response generated by a known agonist and expressed as a percentage of the maximal response of the known agonist. The maximum response caused by a known agonist is defined as a 100% response. Likewise, the maximal response recorded after addition of an agonist to a sample containing a known or test antagonist is detectably lower than the 100% response.

The cells are also useful in reporter gene assays. Reporter gene assays involve the use of host cells transfected with vectors encoding a nucleic acid comprising transcriptional control elements of a target gene (i.e., a gene that controls the biological expression and function of a disease target) spliced to a coding sequence for a reporter gene. Therefore, activation of the target gene results in activation of the reporter gene product. In some embodiments, the reporter gene construct comprises the 5' regulatory region (e.g., promoters and/or enhancers) of a protein whose expression is controlled by SLC18A1 or TAAR2 in operable association with a reporter gene (See Inohara et al., J. Biol. Chem. 275:27823 (2000) for a description of the luciferase reporter construct pBVIx-Luc). Examples of reporter genes finding use in the present invention include, but are not limited to, chloramphenicol transferase, alkaline phosphatase, firefly and bacterial luciferases, β-galactosidase, β-lactamase, and green fluorescent protein. The production of these proteins, with the exception of green fluorescent protein, is detected through the use of chemiluminescent, colorimetric, or bioluminecent products of specific substrates (e.g., X-gal and luciferin). Comparisons between compounds of known and unknown activities may be conducted as described above.

Specifically, the present invention provides screening methods for identifying modulators, i.e., candidate or test compounds or agents (e.g., proteins, peptides, peptidomimetics, peptoids, small molecules or other drugs) which bind to SLC18A1 or TAAR2 of the present invention, have an inhibitory (or stimulatory) effect on, for example, SLC18A1 or TAAR2 expression or SLC18A1 or TAAR2 activity, or have a stimulatory or inhibitory effect on, for example, the expression or activity of a SLC18A1 or TAAR2 substrate. Compounds thus identified can be used to modulate the activity of target gene products (e.g., SLC18A1 or TAAR2 genes) either directly or indirectly in a therapeutic protocol, to elaborate the biological function of the target gene product, or to identify compounds that disrupt normal target gene interactions. Compounds which stimulate the activity of a variant SLC18A1 or variant TAAR2 or mimic the activity of a non-functional variant are particularly useful in the treatment of neuropsychiatric disorders (e.g., schizophrenia).

In one embodiment, the invention provides assays for screening candidate or test compounds that are substrates of a SLC18A1 protein or TAAR2 protein or polypeptide or a biologically active portion thereof. In another embodiment, the invention provides assays for screening candidate or test compounds that bind to or modulate the activity of a SLC18A1 protein or TAAR2 protein or polypeptide or a biologically active portion thereof.

The test compounds of the present invention can be obtained using any of the numerous approaches in combinatorial library methods known in the art, including biological libraries; peptoid libraries (libraries of molecules having the functionalities of peptides, but with a novel, non-peptide backbone, which are resistant to enzymatic degradation but which nevertheless remain bioactive; see, e.g., Zuckermann et al., J. Med. Chem. 37: 2678 (1994)); spatially addressable parallel solid phase or solution phase libraries; synthetic library methods requiring deconvolution; the 'one-bead one-compound' library method; and synthetic library methods using affinity chromatography selection. The biological library and peptoid library approaches are preferred for use with peptide libraries, while the other four approaches are applicable to peptide, non-peptide oligomer or small molecule libraries of compounds (Lam (1997) Anticancer Drug Des. 12:145).

Examples of methods for the synthesis of molecular libraries can be found in the art, for example in: DeWitt et al., Proc. Natl. Acad. Sci. U.S.A. 90:6909 (1993); Erb et al., Proc. Nad. Acad. Sci. USA 91:11422 (1994); Zuckermann et al., J. Med. Chem. 37:2678 (1994); Cho et al., Science 261:1303 (1993); Carrell et al., Angew. Chem. Int. Ed. Engl. 33.2059 (1994); Carell et al., Angew. Chem. Int. Ed. Engl. 33:2061 (1994); and Gallop et al., J. Med. Chem. 37:1233 (1994).

Libraries of compounds may be presented in solution (e.g., Houghten, Biotechniques 13:412-421 (1992)), or on beads (Lam, Nature 354:82-84 (1991)), chips (Fodor, Nature 364:555-556 (1993)), bacteria or spores (U.S. Pat. No. 5,223,409; herein incorporated by reference), plasmids (Cull et al., Proc. Nad. Acad. Sci. USA 89:18651869 (1992)) or on phage (Scott and Smith, Science 249:386-390 (1990); Devlin Science 249:404-406 (1990); Cwirla et al., Proc. Natl. Acad. Sci. 87:6378-6382 (1990); Felici, J. Mol. Biol. 222:301 (1991)).

In one embodiment, an assay is a cell-based assay in which a cell that expresses a SLC18A1 or TAAR2 protein or biologically active portion thereof is contacted with a test compound, and the ability of the test compound to modulate SLC18A1 activity or TAAR2 activity is determined. Determining the ability of the test compound to modulate SLC18A1 activity or TAAR2 activity can be accomplished by monitoring, for example, changes in enzymatic activity. The cell, for example, can be of mammalian origin.

The ability of the test compound to modulate SLC18A1 binding or TAAR2 binding to a compound, e.g., a SLC18A1 substrate or TAAR2 substrate, can also be evaluated. This can be accomplished, for example, by coupling the compound, e.g., the substrate, with a radioisotope or enzymatic label such that binding of the compound, e.g., the substrate, to SLC18A1 or TAAR2 can be determined by detecting the labeled compound, e.g., substrate, in a complex.

Alternatively, the SLC18A1 or TAAR2 is coupled with a radioisotope or enzymatic label to monitor the ability of a test compound to modulate SLC18A1 binding or TAAR2 binding to a SLC18A1 substrate or TAAR2 substrate in a complex. For example, compounds (e.g., substrates) can be labeled with $^{125}I$, $^{35}S^{14}C$ or $^{3}H$, either directly or indirectly, and the radioisotope detected by direct counting of radioemmission or by scintillation counting. Alternatively, compounds can be enzymatically labeled with, for example, horseradish peroxidase, alkaline phosphatase, or luciferase, and the enzymatic label detected by determination of conversion of an appropriate substrate to product.

The ability of a compound (e.g., a SLC18A1 substrate or TAAR2 substrate) to interact with SLC18A1 or TAAR2 with or without the labeling of any of the interactants can be evaluated. For example, a microphysiometer can be used to detect the interaction of a compound with a SLC18A1 or TAAR2 without the labeling of either the compound or the SLC18A1 (McConnell et al. Science 257:1906-1912 (1992)). As used herein, a "microphysiometer" (e.g., Cytosensor) is an analytical instrument that measures the rate at which a cell acidifies its environment using a light-addressable potentiometric sensor (LAPS). Changes in this acidification rate can be used as an indicator of the interaction between a compound and SLC18A1 or TAAR2.

In yet another embodiment, a cell-free assay is provided in which a SLC18A1 protein or TAAR2 protein or biologically active portion thereof is contacted with a test compound and the ability of the test compound to bind to the SLC18A1 protein or TAAR2 protein or a biologically active portion thereof is evaluated. Preferred biologically active portions of the SLC18A1 proteins or TAAR2 proteins to be used in assays of the present invention include fragments that participate in interactions with substrates or other proteins, e.g., fragments with high surface probability scores.

Cell-free assays involve preparing a reaction mixture of the target gene protein and the test compound under conditions and for a time sufficient to allow the two components to interact and bind, thus forming a complex that can be removed and/or detected.

The interaction between two molecules can also be detected, e.g., using fluorescence energy transfer (FRET) (see, for example, Lakowicz et al., U.S. Pat. No. 5,631,169; Stavrianopoulos et al., U.S. Pat. No. 4,968,103; each of which is herein incorporated by reference). A fluorophore label is selected such that a first donor molecule's emitted fluorescent energy will be absorbed by a fluorescent label on a second, 'acceptor' molecule, which in turn is able to fluoresce due to the absorbed energy.

Alternately, the 'donor' protein molecule may simply utilize the natural fluorescent energy of tryptophan residues. Labels are chosen that emit different wavelengths of light, such that the 'acceptor' molecule label may be differentiated from that of the 'donor'. Since the efficiency of energy transfer between the labels is related to the distance separating the molecules, the spatial relationship between the molecules can be assessed. In a situation in which binding occurs between the molecules, the fluorescent emission of the 'acceptor' molecule label in 15 the assay should be maximal. An FRET binding event can be conveniently measured through standard fluorometric detection means well known in the art (e.g., using a fluorimeter).

In another embodiment, determining the ability of the SLC18A1 protein or TAAR2 protein to bind to a target molecule can be accomplished using real-time Biomolecular Interaction Analysis (BIA) (see, e.g., Sjolander and Urbanic-zky, Anal. Chem. 63:2338-2345 (1991) and Szabo et al. Curr. Opin. Struct. Biol. 5:699-705 (1995)). "Surface plasmon resonance" or "BIA" detects biospecific interactions in real time, without labeling any of the interactants (e.g., BIAcore). Changes in the mass at the binding surface (indicative of a binding event) result in alterations of the refractive index of light near the surface (the optical phenomenon of surface plasmon resonance (SPR)), resulting in a detectable signal that can be used as an indication of real-time reactions between biological molecules.

In one embodiment, the target gene product or the test substance is anchored onto a solid phase. The target gene product/test compound complexes anchored on the solid phase can be detected at the end of the reaction. Preferably, the target gene product can be anchored onto a solid surface, and the test compound, (which is not anchored), can be labeled, either directly or indirectly, with detectable labels discussed herein.

It may be desirable to immobilize SLC18A1 or TAAR2, an anti-SLC18A1 or anti-TAAR2 antibody or their target molecules to facilitate separation of complexed from non-complexed forms of one or both of the proteins, as well as to accommodate automation of the assay. Binding of a test compound to a SLC18A1 protein or TAAR2 protein, or interaction of a SLC18A1 protein or TAAR2 protein with a target molecule in the presence and absence of a candidate compound, can be accomplished in any vessel suitable for containing the reactants. Examples of such vessels include microtiter plates, test tubes, and micro-centrifuge tubes. In one embodiment, a fusion protein can be provided that adds a domain that allows one or both of the proteins to be bound to a matrix. For example, glutathione-5-transferase-SLC18A1 or glutathione-5-transferase-TAAR2 fusion proteins or glutathione-5-transferase/target fusion proteins can be adsorbed onto glutathione Sepharose beads (Sigma Chemical, St. Louis, Mo.) or glutathione-derivatized microtiter plates, which are then combined with the test compound or the test compound and either the non-adsorbed target protein or SLC18A1 protein or TAAR2 protein, and the mixture incubated under conditions conducive for complex formation (e.g., at physiological conditions for salt and pH). Following incubation, the beads or microtiter plate wells are washed to remove any unbound components, the matrix immobilized in the case of beads, complex determined either directly or indirectly, for example, as described above.

Alternatively, the complexes can be dissociated from the matrix, and the level of SLC18A1 or TAAR2 binding or activity determined using standard techniques. Other techniques for immobilizing either SLC18A1 protein or TAAR2 protein or a target molecule on matrices include using conjugation of biotin and streptavidin. Biotinylated SLC18A1 or TAAR2 protein or target molecules can be prepared from biotin-NHS(N-hydroxy-succinimide) using techniques known in the art (e.g., biotinylation kit, Pierce Chemicals, Rockford, EL), and immobilized in the wells of streptavidin-coated 96 well plates (Pierce Chemical).

In order to conduct the assay, the non-immobilized component is added to the coated surface containing the anchored component. After the reaction is complete, unreacted components are removed (e.g., by washing) under conditions such that any complexes formed will remain immobilized on the solid surface. The detection of complexes anchored on the solid surface can be accomplished in a number of ways. Where the previously non-immobilized component is pre-labeled, the detection of label immobilized on the surface indicates that complexes were formed. Where the previously non-immobilized component is not pre-labeled, an indirect label can be used to detect complexes anchored on the surface; e.g., using a labeled antibody specific for the immobilized component (the antibody, in turn, can be directly labeled or indirectly labeled with, e.g., a labeled anti-IgG antibody).

This assay is performed utilizing antibodies reactive with SLC18A1 protein or TAAR2 protein or target molecules but which do not interfere with binding of the SLC18A1 protein or TAAR2 protein to its target molecule. Such antibodies can be derivatized to the wells of the plate, and unbound target or SLC18A1 protein or TAAR2 protein trapped in the wells by antibody conjugation. Methods for detecting such complexes, in addition to those described above for the GST-immobilized complexes, include immunodetection of complexes using antibodies reactive with the SLC18A1 protein or TAAR2 protein or target molecule, as well as enzyme-linked assays which rely on detecting an enzymatic activity associated with the SLC18A1 protein or TAAR2 protein or target molecule.

Alternatively, cell free assays can be conducted in a liquid phase. In such an assay, the reaction products are separated from unreacted components, by any of a number of standard techniques, including, but not limited to: differential centrifugation (see, for example, Rivas and Minton, Trends Biochem Sci 18:284-7 (1993)); chromatography (gel filtration chromatography, ion-exchange chromatography); electrophoresis (see, e.g., Ausubel et al., eds. Current Protocols in Molecular Biology 1999, J. Wiley: New York.); and immunoprecipitation (see, for example, Ausubel et al., eds. Current Protocols in Molecular Biology 1999, J. Wiley: New York). Such resins and chromatographic techniques are known to one skilled in the art (See e.g., Heegaard J. Mol. Recognit 11:141-8 (1998); Hageand Tweed J. Chromatogr. Biomed. Sci. Appl 699:499-525 (1997)). Further, fluorescence energy transfer may also be conveniently utilized, as described herein, to detect binding without further purification of the complex from solution.

The assay can include contacting the SLC18A1 protein or TAAR2 protein or biologically active portion thereof with a known compound that binds the SLC18A1 or TAAR2 to form an assay mixture, contacting the assay mixture with a test compound, and determining the ability of the test compound to interact with a SLC18A1 protein or TAAR2 protein, wherein determining the ability of the test compound to interact with a SLC18A1 protein or TAAR2 protein includes determining the ability of the test compound to preferentially bind to SLC18A1 or TAAR2 or biologically active portion thereof, or to modulate the activity of a target molecule, as compared to the known compound.

To the extent that SLC18A1 or TAAR2 can, in vivo, interact with one or more cellular or extracellular macromolecules, such as proteins, inhibitors of such an interaction are useful. A homogeneous assay can be used to identify inhibitors.

For example, a preformed complex of the target gene product and the interactive cellular or extracellular binding partner product is prepared such that either the target gene products or their binding partners are labeled, but the signal generated by the label is quenched due to complex formation (see, e.g., U.S. Pat. No. 4,109,496, herein incorporated by reference, that utilizes this approach for immunoassays). The addition of a test substance that competes with and displaces one of the species from the preformed complex will result in the generation of a signal above background. In this way, test substances that disrupt target gene product-binding partner interaction can be identified. Alternatively, SLC18A1 protein or TAAR2 protein can be used as a "bait protein" in a two-hybrid assay or three-hybrid assay (see, e.g., U.S. Pat. No. 5,283, 317; Zervos et al., Cell 72:223-232 (1993); Madura et al., J. Biol. Chem. 268.12046-12054 (1993); Bartel et al., Biotechniques 14:920-924 (1993); Iwabuchi et al., Oncogene 8:1693-1696 (1993); and Brent WO 94/10300; each of which is herein incorporated by reference), to identify other proteins, that bind to or interact with SLC18A1 or TAAR2 ("SLC18A1-binding proteins" or "SLC18A1-bp" or "TAAR2-binding proteins" or "TAAR2-bp") and are involved in SLC18A1 activity or TAAR2 activity. Such SLC18A1-bps or TAAR2-bps can be activators or inhibitors of signals by the SLC18A1 proteins or TAAR2 proteins or targets as, for example, downstream elements of a SLC18A1-mediated or TAAR2-mediated signaling pathway.

Modulators of SLC18A1 expression or TAAR2 expression can also be identified. For example, a cell or cell free mixture is contacted with a candidate compound and the expression of SLC18A1 mRNA or protein or TAAR2 mRNA or protein evaluated relative to the level of expression of SLC18A1 mRNA or protein or TAAR2 mRNA or protein in the absence of the candidate compound. When expression of SLC18A1 mRNA or protein or TAAR2 mRNA or protein is greater in the presence of the candidate compound than in its absence, the candidate compound is identified as a stimulator of SLC18A1 mRNA or protein or TAAR2 mRNA or protein expression. Alternatively, when expression of SLC18A1 mRNA or protein or TAAR2 mRNA or protein is less (i.e., statistically significantly less) in the presence of the candidate compound than in its absence, the candidate compound is identified as an inhibitor of SLC18A1 mRNA or protein or TAAR2 mRNA or protein expression. The level of SLC18A1 mRNA or protein or TAAR2 mRNA or protein expression can be determined by methods described herein for detecting SLC18A1 mRNA or protein or TAAR2 mRNA or protein.

A modulating agent can be identified using a cell-based or a cell free assay, and the ability of the agent to modulate the activity of a SLC18A1 protein or TAAR2 protein can be confirmed in vivo, e.g., in an animal such as an animal model for a disease (e.g., an animal with neuropsychiatric disease; See e.g., Hildenbrandt and Otto, J. Am. Soc. Nephrol. 11:1753 (2000)).

C. Therapeutic Agents

This invention further pertains to novel agents identified by the above-described screening assays. Accordingly, it is within the scope of this invention to further use an agent identified as described herein (e.g., a SLC18A1 or TAAR2 modulating agent or mimetic, a SLC18A1 or TAAR2 specific antibody, or a SLC18A1 or TAAR2 binding partner) in an appropriate animal model (such as those described herein) to determine the efficacy, toxicity, side effects, or mechanism of action, of treatment with such an agent. Furthermore, novel agents identified by the above-described screening assays can be, e.g., used for treatments of neuropsychiatric disorders (e.g., including, but not limited to, schizophrenia).

VI. Pharmaceutical Compositions Containing SLC18A1 or TAAR2 Nucleic Acid, Peptides, and Analogs The present invention further provides pharmaceutical compositions which may comprise all or portions of SLC18A1 or TAAR2 polynucleotide sequences, SLC18A1 or TAAR2 polypeptides, inhibitors or antagonists of SLC18A1 or TAAR2 bioactivity, including antibodies, alone or in combination with at least one other agent, such as a stabilizing compound, and may be administered in any sterile, biocompatible pharmaceutical carrier, including, but not limited to, saline, buffered saline, dextrose, and water.

The methods of the present invention find use in treating diseases or altering physiological or psychological states characterized by mutant SLC18A1 or TAAR2 alleles (e.g., schizophrenia). Peptides can be administered to the patient intravenously in a pharmaceutically acceptable carrier such as physiological saline. Standard methods for intracellular delivery of peptides can be used (e.g., delivery via liposome). Such methods are well known to those of ordinary skill in the art. The formulations of this invention are useful for parenteral administration, such as intravenous, subcutaneous, intramuscular, and intraperitoneal. Therapeutic administration of a polypeptide intracellularly can also be accomplished using gene therapy as described above.

As is well known in the medical arts, dosages for any one patient depends upon many factors, including the patient's size, body surface area, age, the particular compound to be administered, sex, time and route of administration, general health, and interaction with other drugs being concurrently administered.

Accordingly, in some embodiments of the present invention, SLC18A1 or TAAR2 nucleotide and SLC18A1 or TAAR2 amino acid sequences can be administered to a patient alone, or in combination with other nucleotide sequences, drugs or hormones or in pharmaceutical compositions where it is mixed with excipient(s) or other pharmaceutically acceptable carriers. In one embodiment of the present invention, the pharmaceutically acceptable carrier is pharmaceutically inert. In another embodiment of the present invention, SLC18A1 or TAAR2 polynucleotide sequences or SLC18A1 or TAAR2 amino acid sequences may be administered alone to individuals subject to or suffering from a neuropshychiatric disease.

Depending on the condition being treated, these pharmaceutical compositions may be formulated and administered systemically or locally. Techniques for formulation and administration may be found in the latest edition of "Remington's Pharmaceutical Sciences" (Mack Publishing Co, Easton Pa.). Suitable routes may, for example, include oral or transmucosal administration; as well as parenteral delivery, including intramuscular, subcutaneous, intramedullary, intrathecal, intraventricular, intravenous, intraperitoneal, or intranasal administration.

For injection, the pharmaceutical compositions of the invention may be formulated in aqueous solutions, preferably in physiologically compatible buffers such as Hanks' solution, Ringer's solution, or physiologically buffered saline. For tissue or cellular administration, penetrants appropriate to the particular barrier to be permeated are used in the formulation. Such penetrants are generally known in the art.

In other embodiments, the pharmaceutical compositions of the present invention can be formulated using pharmaceutically acceptable carriers well known in the art in dosages suitable for oral administration. Such carriers enable the pharmaceutical compositions to be formulated as tablets, pills, capsules, liquids, gels, syrups, slurries, suspensions and the like, for oral or nasal ingestion by a patient to be treated.

Pharmaceutical compositions suitable for use in the present invention include compositions wherein the active ingredients are contained in an effective amount to achieve the intended purpose. For example, an effective amount of SLC18A1 or TAAR2 may be that amount that suppresses apoptosis. Determination of effective amounts is well within the capability of those skilled in the art, especially in light of the disclosure provided herein.

In addition to the active ingredients these pharmaceutical compositions may contain suitable pharmaceutically acceptable carriers comprising excipients and auxiliaries that facilitate processing of the active compounds into preparations that can be used pharmaceutically. The preparations formulated for oral administration may be in the form of tablets, dragees, capsules, or solutions.

The pharmaceutical compositions of the present invention may be manufactured in a manner that is itself known (e.g., by means of conventional mixing, dissolving, granulating, dragee-making, levigating, emulsifying, encapsulating, entrapping or lyophilizing processes).

Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances that increase the viscosity of the suspension, such as sodium carboxymethyl cellulose, sorbitol, or dextran. Optionally, the suspension may also contain suitable stabilizers or agents that increase the solubility of the compounds to allow for the preparation of highly concentrated solutions.

Pharmaceutical preparations for oral use can be obtained by combining the active compounds with solid excipient, optionally grinding a resulting mixture, and processing the mixture of granules, after adding suitable auxiliaries, if desired, to obtain tablets or dragee cores. Suitable excipients are carbohydrate or protein fillers such as sugars, including lactose, sucrose, mannitol, or sorbitol; starch from corn, wheat, rice, potato, etc; cellulose such as methyl cellulose, hydroxypropylmethyl-cellulose, or sodium carboxymethylcellulose; and gums including arabic and tragacanth; and proteins such as gelatin and collagen. If desired, disintegrating or solubilizing agents may be added, such as the cross-linked polyvinyl pyrrolidone, agar, alginic acid or a salt thereof such as sodium alginate.

Dragee cores are provided with suitable coatings such as concentrated sugar solutions, which may also contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for product identification or to characterize the quantity of active compound, (i.e., dosage).

Pharmaceutical preparations that can be used orally include push-fit capsules made of gelatin, as well as soft, sealed capsules made of gelatin and a coating such as glycerol or sorbitol. The push-fit capsules can contain the active ingredients mixed with a filler or binders such as lactose or starches, lubricants such as talc or magnesium stearate, and, optionally, stabilizers. In soft capsules, the active compounds may be dissolved or suspended in suitable liquids, such as fatty oils, liquid paraffin, or liquid polyethylene glycol with or without stabilizers.

Compositions comprising a compound of the invention formulated in a pharmaceutical acceptable carrier may be prepared, placed in an appropriate container, and labeled for treatment of an indicated condition. For polynucleotide or amino acid sequences of SLC18A1 or TAAR2, conditions indicated on the label may include treatment of condition related to neurotransmitter signaling.

The pharmaceutical composition may be provided as a salt and can be formed with many acids, including but not limited to hydrochloric, sulfuric, acetic, lactic, tartaric, malic, succinic, etc. Salts tend to be more soluble in aqueous or other protonic solvents that are the corresponding free base forms. In other cases, the preferred preparation may be a lyophilized powder in 1 mM-50 mM histidine, 0.1%-2% sucrose, 2%-7% mannitol at a pH range of 4.5 to 5.5 that is combined with buffer prior to use.

For any compound used in the method of the invention, the therapeutically effective dose can be estimated initially from cell culture assays. Then, preferably, dosage can be formulated in animal models (particularly murine models) to achieve a desirable circulating concentration range that adjusts SLC18A1 or TAAR2 levels.

A therapeutically effective dose refers to that amount of SLC18A1 or TAAR2 that ameliorates symptoms of the disease state. Toxicity and therapeutic efficacy of such compounds can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index, and it can be expressed as the ratio $LD_{50}/ED_{50}$. Compounds that exhibit large therapeutic indices are preferred. The data obtained from these cell culture assays and additional animal studies can be used in formulating a range of dosage for human use. The dosage of such compounds lies preferably within a range of circulating concentrations that include the $ED_{50}$ with little or no toxicity. The dosage varies within this range depending upon the dosage form employed, sensitivity of the patient, and the route of administration.

The exact dosage is chosen by the individual physician in view of the patient to be treated. Dosage and administration are adjusted to provide sufficient levels of the active moiety or to maintain the desired effect. Additional factors which may be taken into account include the severity of the disease state; age, weight, and gender of the patient; diet, time and frequency of administration, drug combination(s), reaction sensitivities, and tolerance/response to therapy. Long acting pharmaceutical compositions might be administered every 3 to 4 days, every week, or once every two weeks depending on half-life and clearance rate of the particular formulation.

Normal dosage amounts may vary from 0.1 to 100,000 micrograms, up to a total dose of about 1 g, depending upon the route of administration. Guidance as to particular dosages and methods of delivery is provided in the literature (See, U.S. Pat. Nos. 4,657,760; 5,206,344; or 5,225,212, all of which are herein incorporated by reference). Those skilled in the art will employ different formulations for SLC18A1 or TAAR2 than for the inhibitors of SLC18A1 or TAAR2. Administration to the bone marrow may necessitate delivery in a manner different from intravenous injections.

6. Variants of SLC18A1 or TAAR2

Still other embodiments of the present invention provide mutant or variant forms of SLC18A1 or TAAR2 (i.e., muteins). It is possible to modify the structure of a peptide having an activity of SLC18A1 or TAAR2 for such purposes as enhancing therapeutic or prophylactic efficacy, or stability (e.g., ex vivo shelf life, and/or resistance to proteolytic degradation in vivo). Such modified peptides are considered functional equivalents of peptides having an activity of the subject SLC18A1 or TAAR2 proteins as defined herein. A modified peptide can be produced in which the amino acid sequence has been altered, such as by amino acid substitution, deletion, or addition.

Moreover, as described above, variant forms (e.g., mutants or polymorphic sequences) of the subject SLC18A1 or TAAR2 proteins are also contemplated as being equivalent to those peptides and DNA molecules that are set forth in more detail. For example, as described above, the present invention encompasses mutant and variant proteins that contain conservative or non-conservative amino acid substitutions.

This invention further contemplates a method of generating sets of combinatorial mutants of the present SLC18A1 or TAAR2 proteins, as well as truncation mutants, and is especially useful for identifying potential variant sequences (i.e., mutants or polymorphic sequences) that are involved in neuropsychiatric disorders or resistance to neuropsychiatric disorders. The purpose of screening such combinatorial libraries is to generate, for example, novel SLC18A1 or TAAR2 variants that can act as either agonists or antagonists, or alternatively, possess novel activities all together.

Therefore, in some embodiments of the present invention, SLC18A1 or TAAR2 variants are engineered by the present method to provide altered (e.g., increased or decreased) biological activity. In other embodiments of the present invention, combinatorially-derived variants are generated which have a selective potency relative to a naturally occurring SLC18A1 or TAAR2. Such proteins, when expressed from recombinant DNA constructs, can be used in gene therapy protocols.

Still other embodiments of the present invention provide SLC18A1 or TAAR2 variants that have intracellular half-lives dramatically different than the corresponding wild-type protein. For example, the altered protein can be rendered either more stable or less stable to proteolytic degradation or other cellular process that result in destruction of, or otherwise inactivate SLC18A1 or TAAR2. Such variants, and the genes which encode them, can be utilized to alter the location of SLC18A1 or TAAR2 expression by modulating the half-life of the protein. For instance, a short half-life can give rise to more transient SLC18A1 or TAAR2 biological effects and, when part of an inducible expression system, can allow tighter control of SLC18A1 or TAAR2 levels within the cell. As above, such proteins, and particularly their recombinant nucleic acid constructs, can be used in gene therapy protocols.

In still other embodiments of the present invention, SLC18A1 or TAAR2 variants are generated by the combinatorial approach to act as antagonists, in that they are able to interfere with the ability of the corresponding wild-type protein to regulate cell function.

In some embodiments of the combinatorial mutagenesis approach of the present invention, the amino acid sequences for a population of SLC18A1 or TAAR2 homologs, variants or other related proteins are aligned, preferably to promote the highest homology possible. Such a population of variants can include, for example, SLC18A1 or TAAR2 homologs from one or more species, or SLC18A1 or TAAR2 variants from the same species but which differ due to mutation or polymorphisms. Amino acids that appear at each position of the aligned sequences are selected to create a degenerate set of combinatorial sequences.

In a preferred embodiment of the present invention, the combinatorial SLC18A1 or TAAR2 library is produced by way of a degenerate library of genes encoding a library of polypeptides which each include at least a portion of potential SLC18A1 or TAAR2 protein sequences. For example, a mixture of synthetic oligonucleotides can be enzymatically ligated into gene sequences such that the degenerate set of potential SLC18A1 or TAAR2 sequences are expressible as individual polypeptides, or alternatively, as a set of larger fusion proteins (e.g., for phage display) containing the set of SLC18A1 or TAAR2 sequences therein.

There are many ways by which the library of potential SLC18A1 or TAAR2 homologs and variants can be generated from a degenerate oligonucleotide sequence. In some embodiments, chemical synthesis of a degenerate gene sequence is carried out in an automatic DNA synthesizer, and the synthetic genes are ligated into an appropriate gene for expression. The purpose of a degenerate set of genes is to provide, in one mixture, all of the sequences encoding the desired set of potential SLC18A1 or TAAR2 sequences. The synthesis of degenerate oligonucleotides is well known in the art (See e.g., Narang, Tetrahedron Lett., 39:39 (1983); Itakura et al., Recombinant DNA, in Walton (ed.), *Proceedings of the 3 rd Cleveland Symposium on Macromolecules*, Elsevier, Amsterdam, pp 273-289 (1981); Itakura et al., Annu. Rev. Biochem., 53:323 (1984); Itakura et al., Science 198:1056 (1984); Ike et al., Nucl. Acid Res., 11:477 (1983)). Such techniques have been employed in the directed evolution of other proteins (See e.g., Scott et al., Science 249:386 (1980); Roberts et al., Proc. Natl. Acad. Sci. USA 89:2429 (1992); Devlin et al., Science 249: 404 (1990); Cwirla et al., Proc. Natl. Acad. Sci. USA 87: 6378 (1990); each of which is herein incorporated by reference; as well as U.S. Pat. Nos. 5,223,409, 5,198,346, and 5,096,815; each of which is incorporated herein by reference).

It is contemplated that the SLC18A1 or TAAR2 nucleic acids (e.g., SEQ ID NOS: 1-4, and fragments and variants thereof) can be utilized as starting nucleic acids for directed evolution. These techniques can be utilized to develop SLC18A1 or TAAR2 variants having desirable properties such as increased or decreased biological activity.

In some embodiments, artificial evolution is performed by random mutagenesis (e.g., by utilizing error-prone PCR to introduce random mutations into a given coding sequence). This method requires that the frequency of mutation be finely tuned. As a general rule, beneficial mutations are rare, while deleterious mutations are common. This is because the combination of a deleterious mutation and a beneficial mutation often results in an inactive enzyme. The ideal number of base substitutions for targeted gene is usually between 1.5 and 5 (Moore and Arnold, Nat. Biotech., 14, 458 (1996); Leung et al., Technique, 1:11 (1989); Eckert and Kunkel, PCR Methods Appl., 1:17-24 (1991); Caldwell and Joyce, PCR Methods Appl., 2:28 (1992); and Zhao and Arnold, Nuc. Acids. Res., 25:1307 (1997)). After mutagenesis, the resulting clones are selected for desirable activity (e.g., screened for SLC18A1 activity). Successive rounds of mutagenesis and selection are often necessary to develop enzymes with desirable properties. It should be noted that only the useful mutations are carried over to the next round of mutagenesis.

In other embodiments of the present invention, the polynucleotides of the present invention are used in gene shuffling or sexual PCR procedures (e.g., Smith, Nature, 370:324 (1994); U.S. Pat. Nos. 5,837,458; 5,830,721; 5,811,238; 5,733,731; all of which are herein incorporated by reference). Gene shuffling involves random fragmentation of several mutant DNAs followed by their reassembly by PCR into full length molecules. Examples of various gene shuffling procedures include, but are not limited to, assembly following DNase treatment, the staggered extension process (STEP), and random priming in vitro recombination. In the DNase mediated method, DNA segments isolated from a pool of positive mutants are cleaved into random fragments with DNaseI and subjected to multiple rounds of PCR with no added primer. The lengths of random fragments approach that of the uncleaved segment as the PCR cycles proceed, resulting in mutations in present in different clones becoming mixed and accumulating in some of the resulting sequences. Multiple cycles of selection and shuffling have led to the functional enhancement of several enzymes (Stemmer, Nature, 370:398 (1994); Stemmer, Proc. Natl. Acad. Sci. USA, 91:10747 (1994); Crameri et al., Nat. Biotech., 14:315 (1996); Zhang et al., Proc. Natl. Acad. Sci. USA, 94:4504 (1997); and Crameri et al., Nat. Biotech., 15:436 (1997)). Variants produced by directed evolution can be screened for SLC18A1 activity by the methods described herein.

A wide range of techniques are known in the art for screening gene products of combinatorial libraries made by point mutations, and for screening cDNA libraries for gene products having a certain property. Such techniques will be generally adaptable for rapid screening of the gene libraries generated by the combinatorial mutagenesis or recombination of SLC18A1 or TAAR2 homologs or variants. The most widely used techniques for screening large gene libraries typically comprises cloning the gene library into replicable expression vectors, transforming appropriate cells with the resulting library of vectors, and expressing the combinatorial genes under conditions in which detection of a desired activity facilitates relatively easy isolation of the vector encoding the gene whose product was detected.

7. Chemical Synthesis of SLC18A1 or TAAR2

In an alternate embodiment of the invention, the coding sequence of SLC18A1 or TAAR2 is synthesized, whole or in part, using chemical methods well known in the art (See e.g., Caruthers et al., Nucl. Acids Res. Symp. Ser., 7:215 (1980); Crea and Horn, Nucl. Acids Res., 9:2331 (1980); Matteucci and Caruthers, Tetrahedron Lett., 21:719 (1980); and Chow and Kempe, Nucl. Acids Res., 9:2807 (1981)). In other embodiments of the present invention, the protein itself is produced using chemical methods to synthesize either an entire SLC18A1 or TAAR2 amino acid sequence or a portion thereof. For example, peptides can be synthesized by solid phase techniques, cleaved from the resin, and purified by preparative high performance liquid chromatography (See e.g., Creighton, *Proteins Structures And Molecular Principles*, W H Freeman and Co, New York N.Y. (1983)). In other embodiments of the present invention, the composition of the synthetic peptides is confirmed by amino acid analysis or sequencing (See e.g., Creighton, supra).

Direct peptide synthesis can be performed using various solid-phase techniques (Roberge et al., Science 269:202 (1995)) and automated synthesis may be achieved, for example, using ABI 431 A Peptide Synthesizer (Perkin Elmer) in accordance with the instructions provided by the manufacturer. Additionally, the amino acid sequence of SLC18A1 or TAAR2, or any part thereof, may be altered during direct synthesis and/or combined using chemical methods with other sequences to produce a variant polypeptide.

EXPERIMENTAL

The following examples are provided in order to demonstrate and further illustrate certain preferred embodiments and aspects of the present invention and are not to be construed as limiting the scope thereof.

Example 1

Materials and Methods

DNA was obtained from postmortem brain tissue from 28 unrelated Caucasian schizophrenics (23 (18 males, 5 females) from the Stanley Medical Research Institute (Bethesda, Md.) and 5 (4 males, 1 female) from Asterand, Inc. (Detroit, Mich.)) and from whole blood from 38 unrelated and unaffected Caucasians (29 males, 9 females) (Golden West Biologicals (Temecula, Calif.). Appropriate institute review board approval was obtained. Protein encoding exon regions for SLC18A1 and TAAR2 were PCR amplified and DNA sequenced.

Example 2

Identification of SLC18A1 as a Biomarker of Neuropsychiatric Disorders

A missense homozygous mutation in exon 3 of SLC18A1 (A277C resulting in T4P) was identified and determined to be statistically significant (p value (2-tail)=0.036 with Fisher's Exact Test) within the neuropsychiatric diseased group versus the control group. Wild type SLC18A1, nucleotides 271-280, is shown in SEQ ID NO. 1 below. Mutant SLC18A1, nucleotides 271-280, is shown in SEQ ID NO. 2 below.

SEQ ID NO. 1: 5'-ctccggacca-3'

SEQ ID NO. 2: 5'-ctccggccca-3'

Allelic variations are shown in Table 1, below.

TABLE 1

Frequency of SLC18A1 genotypes at A277C (resulting in T4P) in individuals for schizophrenic and control groups

| Genotype | Schizophrenic group frequency (%) (n = 28 (22 males)) | Control group frequency (%) (n = 38 (29 males)) |
| --- | --- | --- |
| C/C | 21.4 | 2.6 |
| A/C | 50.0 | 23.7 |
| A/A | 28.6 | 73.6 |

The C/C genotype, corresponding to a proline residue in the protein, occurred in 21.4% of the schizophrenic group and in only 2.6% of the control group. Thus, in some embodiments, the A277C mutation in SLC18A1 exists as a diagnostic marker for neuorpsychiatric disease (e.g., schizophrenia). The A/A genotype, corresponding to a threonine residue in the protein, occurred in only 28.6% of the diseased group and in the majority of the control group. The Hardy-Weinberg value was 1.00. Nucleotide positions are numbered according to GenBank accession number NM_003053. From the predicted secondary structure (Hayashi et al., 1999 J. Neurochem. 73, 2538-2545), the first 21 amino acid residues are outside of the transmembrane domains. The observed mutation in residue 4 changes threonine, with an aliphatic hydroxyl group, to proline, with a secondary amine group. Although a mechanism is not required for practicing the present invention, and the invention is not limited to any particular mechanism, in some embodiments, it is contemplated that presence of the amino acid substitution of T4P leads to an uptake and/or release of serotonin.

Example 3

Identification of TAAR2 as a Biomarker of Neuropsychiatric Disorders

A missense homozygous mutation in exon 2 of TAAR2 (A214G resulting in S36G)) was identified as statistically significant within the neuropsychiatric disease group versus controls. Wild type TAAR2, nucleotides 211-220, is shown in SEQ ID NO. 3 below. Mutant TAAR2, nucleotides 211-220, is shown in SEQ ID NO. 4 below.

```
SEQ ID NO. 3: 5'-tgcaagattt-3', Wild type TAAR2,
nucleotides 211-220.

SEQ ID NO. 4: 5'-tgcgagattt-3', Mutant TAAR2,
nucleotides 211-220.
```

Allelic variations of the samples are shown in Table 2. The G/G genotype, corresponding to a serine residue in place of glycine in the protein, occurred in 14.8% of the schizophrenic group and in only 5.3% of the control group. Thus, in some embodiments, a A213G mutation in TAAR2 exists as a diagnostic marker for neuropsychiatric disease (e.g., schizophrenia). Alternatively, the A/A genotype, corresponding to a glycine residue in the protein, occurred in 40.7% of the diseased group and in 40.8% of the control group. Nucleotide positions are numbered according to GenBank accession number NM_014626.

TABLE 2

Frequency of TAAR2 genotypes in individuals for schizophrenic and control groups.

| Genotype | Schizophrenic Group Frequency (%) (n = 28 (22 males)) | Control Group Frequency (%) (n = 56 (? males)) |
|---|---|---|
| G/A | 10.7 | 5.5 |
| G/G | 89.3 | 94.5 |
| A/A | 0.0 | 0.0 |

All publications and patents mentioned in the above specification are herein incorporated by reference. Various modifications and variations of the described compositions and methods of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention that are obvious to those skilled in the relevant fields are intended to be within the scope of the present invention.

---

I claim:

1. A method for identifying an increased susceptibility to schizophrenia comprising detecting an A277C mutation in an SLC18A1 nucleic acid sequence in a sample from a human female subject, and identifying said subject as having an increased susceptibility to schizophrenia.

2. The method of claim 1, wherein said detecting comprises determining the presence of SEQ ID NO: 2.

3. The method of claim 1, wherein said subject is determined to be homozygous for said A277C mutation.

* * * * *

SEQUENCE LISTING

```
<160> NUMBER OF SEQ ID NOS: 8

<210> SEQ ID NO 1
<211> LENGTH: 10
<212> TYPE: DNA
<213> ORGANISM: Artificial Sequence
<220> FEATURE:
<223> OTHER INFORMATION: Synthetic

<400> SEQUENCE: 1
ctccggacca                                                           10

<210> SEQ ID NO 2
<211> LENGTH: 10
<212> TYPE: DNA
<213> ORGANISM: Artificial Sequence
<220> FEATURE:
<223> OTHER INFORMATION: Synthetic

<400> SEQUENCE: 2
ctccggccca                                                           10

<210> SEQ ID NO 3
<211> LENGTH: 10
<212> TYPE: DNA
<213> ORGANISM: Artificial Sequence
<220> FEATURE:
<223> OTHER INFORMATION: Synthetic

<400> SEQUENCE: 3
tgcaagattt                                                           10

<210> SEQ ID NO 4
<211> LENGTH: 10
<212> TYPE: DNA
```

<213> ORGANISM: Artificial Sequence
<220> FEATURE:
<223> OTHER INFORMATION: Synthetic

<400> SEQUENCE: 4
tgcgagattt                                                           10

<210> SEQ ID NO 5
<211> LENGTH: 2749
<212> TYPE: DNA
<213> ORGANISM: Homo sapiens

<400> SEQUENCE: 5

| | | | | | |
|---|---|---|---|---|---|
| cacacacaca | catacacaga | atcctcagat | aacaggaggc | aataaatcca | acagcacatc | 60 |
| cacgttcaga | gaacagtgtc | cctgctgtct | tgctaacagc | tgccaatacc | tcactgagtg | 120 |
| cctcacacca | acatgggctc | caagtgagtt | tccttcgtct | gggcagactc | cctcccctct | 180 |
| tccataaagg | ctgcaggaga | cctgtagctg | tcacaggacc | ttccctaaga | gcccgcaggg | 240 |
| aaagactgcc | ccagtccggc | catcaccatg | ctccggacca | ttctggatgc | tccccagcgg | 300 |
| ttgctgaagg | aggggagagc | gtcccggcag | ctggtgctgg | tggtggtatt | cgtcgctttg | 360 |
| ctcctggaca | acatgctgtt | tactgtggtg | gtgccaattg | tgcccacctt | cctatatgac | 420 |
| atggagttca | agaagtcaa | ctcttctctg | cacctcggcc | atgccggaag | ttccccacat | 480 |
| gccctcgcct | ctcctgcctt | ttccaccatc | ttctccttct | tcaacaacaa | caccgtggct | 540 |
| gttgaagaaa | gcgtacctag | tggaatagca | tggatgaatg | acactgccag | caccatccca | 600 |
| cctccagcca | ctgaagccat | ctcagctcat | aaaaacaact | gcttgcaagg | cacaggtttc | 660 |
| ttggaggaag | agattacccg | ggtcgggggtt | ctgtttgctt | caaaggctgt | gatgcaactt | 720 |
| ctggtcaacc | cattcgtggg | ccctctcacc | aacaggatta | gatatcatat | ccccatgttt | 780 |
| gctggctttg | ttatcatgtt | tctctccaca | gttatgtttg | cttttttctgg | gacctatact | 840 |
| ctactctttg | tggcccgaac | ccttcaaggc | attggatctt | cattttcatc | tgttgcaggt | 900 |
| cttgaatgc | tggccagtgt | ctacactgat | gaccatgaga | gaggacgagc | catgggaact | 960 |
| gctctggggg | gcctggcctt | ggggttgctg | gtgggagctc | cctttggaag | tgtaatgtac | 1020 |
| gagtttgttg | ggaagtctgc | acccttcctc | atcctggcct | tcctggcact | actggatgga | 1080 |
| gcactccagc | tttgcatcct | acagccttcc | aaagtctctc | ctgagagtgc | caaggggact | 1140 |
| cccctctttta | tgcttctcaa | agacccttac | atcctggtgg | ctgcagggtc | catctgcttt | 1200 |
| gccaacatgg | gggtggccat | cctggagccc | acactgccca | tctggatgat | gcagaccatg | 1260 |
| tgctccccca | agtggcagct | gggtctagct | ttcttgcctg | ccagtgtgtc | ctacctcatt | 1320 |
| ggcaccaacc | tctttggtgt | gttggccaac | aagatgggtc | ggtggctgtg | ttccctaatc | 1380 |
| gggatgctgg | tagtaggtac | cagcttgctc | tgtgttcctc | tggctcacaa | tattttggt | 1440 |
| ctcattggcc | ccaatgcagg | gcttggcctt | gccataggca | tggtggattc | ttctatgatg | 1500 |
| cccatcatgg | ggcacctggt | ggatctacgc | cacacctcgg | tgtatgggag | tgtctacgcc | 1560 |
| atcgctgatg | tggcttttttg | catgggctttt | gctataggtc | catccaccgg | tggtgccatt | 1620 |
| gtaaaggcca | tcggttttcc | ctggctcatg | gtcatcactg | gggtcatcaa | catcgtctat | 1680 |
| gctccactct | gctactacct | gcggagcccc | ccggcaaagg | aagagaagct | tgctattctg | 1740 |
| agtcaggact | gccccatgga | gacccggatg | tatgcaaccc | agaagcccac | gaaggaattt | 1800 |
| cctctgggggg | aggacagtga | tgaggagcct | gaccatgagg | agtagcagca | gaaggtgctc | 1860 |
| cttgaattca | tgatgcctca | gtgaccacct | ctttccctgg | gaccagatca | ccatggctga | 1920 |

-continued

```
gcccacggct cagtgggctt cacatacctc tgcctgggaa tcttctttcc tcccctccca   1980
tggacactgt ccctgatact cttctcacct gtgtaacttg tagctcttcc tctatgcctt   2040
ggtgccgcag tggcccatct tttatgggaa gacagagtga tgcaccttcc cgctgctgtg   2100
aggttgatta aacttgagct gtgacgggtt ctgcaagggg tgactcattg catagaggtg   2160
gtagtgagta atgtgcccct gaaaccagtg gggtgactga caagcctctt taatctgttg   2220
cctgattttc tctggcatag tcccaacaga tcggaagagt gttaccctct tttcctcaac   2280
gtgttctttc ccgggttttc ccagccgagt tgagaaaatg ttctcagcat tgtcttgctg   2340
ccaaatgcca gcttgaagag ttttgttttg ttttttttcc atttattttt ttttttaat    2400 aaagtgagtg atttttctgt ggctaaatct agagctgcta aaagggcttt accctcagtg   2460
aaaagtgtct tctattttca ttatctttca gaaacaggag cccatttctc ttctgctgga   2520
gttattgaca ttctcctgac ctcccctgtg tgttcctacc ttttctgaac ctcttagact   2580
cttagaaata aaagtagaag aaagacagaa aaaataactg attagaccca agatttcatg   2640
ggaagaagtt aaaagaaact gccttgaaat ccctcctgat tgtagatttc ctaataggag   2700
gggtgtaatg tgacattgtt catacttgct aataaataca ttattgcct               2749
```

<210> SEQ ID NO 6
<211> LENGTH: 525
<212> TYPE: PRT
<213> ORGANISM: Homo sapiens

<400> SEQUENCE: 6

```
Met Leu Arg Thr Ile Leu Asp Ala Pro Gln Arg Leu Leu Lys Glu Gly
1               5                  10                  15

Arg Ala Ser Arg Gln Leu Val Leu Val Val Phe Val Ala Leu Leu
            20                  25                  30

Leu Asp Asn Met Leu Phe Thr Val Val Pro Ile Val Pro Thr Phe
        35                  40                  45

Leu Tyr Asp Met Glu Phe Lys Glu Val Asn Ser Ser Leu His Leu Gly
    50                  55                  60

His Ala Gly Ser Ser Pro His Ala Leu Ala Ser Pro Ala Phe Ser Thr
65                  70                  75                  80

Ile Phe Ser Phe Phe Asn Asn Asn Thr Val Ala Val Glu Glu Ser Val
                85                  90                  95

Pro Ser Gly Ile Ala Trp Met Asn Asp Thr Ala Ser Thr Ile Pro Pro
            100                 105                 110

Pro Ala Thr Glu Ala Ile Ser Ala His Lys Asn Asn Cys Leu Gln Gly
        115                 120                 125

Thr Gly Phe Leu Glu Glu Glu Ile Thr Arg Val Gly Val Leu Phe Ala
    130                 135                 140

Ser Lys Ala Val Met Gln Leu Leu Val Asn Pro Phe Val Gly Pro Leu
145                 150                 155                 160

Thr Asn Arg Ile Gly Tyr His Ile Pro Met Phe Ala Gly Phe Val Ile
                165                 170                 175

Met Phe Leu Ser Thr Val Met Phe Ala Phe Ser Gly Tyr Thr Leu
            180                 185                 190

Leu Phe Val Ala Arg Thr Leu Gln Gly Ile Gly Ser Ser Phe Ser Ser
        195                 200                 205

Val Ala Gly Leu Gly Met Leu Ala Ser Val Tyr Thr Asp Asp His Glu
    210                 215                 220

Arg Gly Arg Ala Met Gly Thr Ala Leu Gly Gly Leu Ala Leu Gly Leu
225                 230                 235                 240
```

Leu Val Gly Ala Pro Phe Gly Ser Val Met Tyr Glu Phe Val Gly Lys
             245                 250                 255

Ser Ala Pro Phe Leu Ile Leu Ala Phe Leu Ala Leu Leu Asp Gly Ala
             260                 265                 270

Leu Gln Leu Cys Ile Leu Gln Pro Ser Lys Val Ser Pro Glu Ser Ala
         275                 280                 285

Lys Gly Thr Pro Leu Phe Met Leu Leu Lys Asp Pro Tyr Ile Leu Val
     290                 295                 300

Ala Ala Gly Ser Ile Cys Phe Ala Asn Met Gly Val Ala Ile Leu Glu
305                 310                 315                 320

Pro Thr Leu Pro Ile Trp Met Met Gln Thr Met Cys Ser Pro Lys Trp
                 325                 330                 335

Gln Leu Gly Leu Ala Phe Leu Pro Ala Ser Val Ser Tyr Leu Ile Gly
             340                 345                 350

Thr Asn Leu Phe Gly Val Leu Ala Asn Lys Met Gly Arg Trp Leu Cys
         355                 360                 365

Ser Leu Ile Gly Met Leu Val Val Gly Thr Ser Leu Leu Cys Val Pro
     370                 375                 380

Leu Ala His Asn Ile Phe Gly Leu Ile Gly Pro Asn Ala Gly Leu Gly
385                 390                 395                 400

Leu Ala Ile Gly Met Val Asp Ser Ser Met Met Pro Ile Met Gly His
                 405                 410                 415

Leu Val Asp Leu Arg His Thr Ser Val Tyr Gly Ser Val Tyr Ala Ile
             420                 425                 430

Ala Asp Val Ala Phe Cys Met Gly Phe Ala Ile Gly Pro Ser Thr Gly
         435                 440                 445

Gly Ala Ile Val Lys Ala Ile Gly Phe Pro Trp Leu Met Val Ile Thr
     450                 455                 460

Gly Val Ile Asn Ile Val Tyr Ala Pro Leu Cys Tyr Tyr Leu Arg Ser
465                 470                 475                 480

Pro Pro Ala Lys Glu Glu Lys Leu Ala Ile Leu Ser Gln Asp Cys Pro
                 485                 490                 495

Met Glu Thr Arg Met Tyr Ala Thr Gln Lys Pro Thr Lys Glu Phe Pro
             500                 505                 510

Leu Gly Glu Asp Ser Asp Glu Glu Pro Asp His Glu Glu
         515                 520                 525

<210> SEQ ID NO 7
<211> LENGTH: 921
<212> TYPE: DNA
<213> ORGANISM: Homo sapiens

<400> SEQUENCE: 7
atgtattcat ttatggcagg atccatattc atcacaatat tggcaatctt tgccatgata      60
atttccattt cctacttcaa gcagcttcac acaccaacca acttcctcat cctctccatg     120
gccatcactg atttcctcct gggattcacc atcatgccat atagtatgat cagatcggtg     180
gagaactgct ggtattttgg gcttacattt tgcaagattt attatagttt tgacctgatg     240
cttagcataa catccatttt tcatctttgc tcagtggcca ttgatagatt ttatgctata     300
tgttacccat tactttattc caccaaaata actattccag tcattaaaag attgctactt     360
ctatgttggt cggtccctgg agcatttgcc ttcggggtgg tcttctcaga ggcctatgca     420
gatggaaata gagggctatga catccttggtt gcttgttcca gttcctgccc agtgatgttc     480
aacaagctat gggggaccac cttgtttatg gcaggtttct tcactcctgg gtctatgatg     540
gtggggattt atggcaaaat ttttgcagta tccagaaaac atgctcatgc catcaataac    600
ttgcgagaaa atcaaaataa tcaagtgaag aaagacaaaa aagctgccaa aactttagga    660
atagtgatag gagttttctt attatgttgg tttccttgtt tcttcacaat tttattggat    720 cccttttga acttctctac tcctgtagtt ttgtttgatg ccttgacatg gtttggctat    780
tttaactcca catgtaatcc gttaatatat ggtttcttct atccctggtt tcgcagagca    840
ctgaagtaca ttttgctagg taaaattttc agctcatgtt tccataatac tattttgtgt    900
atgcaaaaag aaagtgagta g    921

<210> SEQ ID NO 8
<211> LENGTH: 306
<212> TYPE: PRT
<213> ORGANISM: Homo sapiens

<400> SEQUENCE: 8

Met Tyr Ser Phe Met Ala Gly Ser Ile Phe Ile Thr Ile Phe Gly Asn
1               5                   10                  15

Leu Ala Met Ile Ile Ser Ile Ser Tyr Phe Lys Gln Leu His Thr Pro
            20                  25                  30

Thr Asn Phe Leu Ile Leu Ser Met Ala Ile Thr Asp Phe Leu Leu Gly
        35                  40                  45

Phe Thr Ile Met Pro Tyr Ser Met Ile Arg Ser Val Glu Asn Cys Trp
    50                  55                  60

Tyr Phe Gly Leu Thr Phe Cys Lys Ile Tyr Tyr Ser Phe Asp Leu Met
65                  70                  75                  80

Leu Ser Ile Thr Ser Ile Phe His Leu Cys Ser Val Ala Ile Asp Arg
                85                  90                  95

Phe Tyr Ala Ile Cys Tyr Pro Leu Leu Tyr Ser Thr Lys Ile Thr Ile
            100                 105                 110

Pro Val Ile Lys Arg Leu Leu Leu Leu Cys Trp Ser Val Pro Gly Ala
        115                 120                 125

Phe Ala Phe Gly Val Val Phe Ser Glu Ala Tyr Ala Asp Gly Ile Glu
    130                 135                 140

Gly Tyr Asp Ile Leu Val Ala Cys Ser Ser Ser Cys Pro Val Met Phe
145                 150                 155                 160

Asn Lys Leu Trp Gly Thr Thr Leu Phe Met Ala Gly Phe Phe Thr Pro
                165                 170                 175

Gly Ser Met Met Val Gly Ile Tyr Gly Lys Ile Phe Ala Val Ser Arg
            180                 185                 190

Lys His Ala His Ala Ile Asn Asn Leu Arg Glu Asn Gln Asn Asn Gln
        195                 200                 205

Val Lys Lys Asp Lys Lys Ala Ala Lys Thr Leu Gly Ile Val Ile Gly
    210                 215                 220

Val Phe Leu Leu Cys Trp Phe Pro Cys Phe Phe Thr Ile Leu Leu Asp
225                 230                 235                 240

Pro Phe Leu Asn Phe Ser Thr Pro Val Val Leu Phe Asp Ala Leu Thr
                245                 250                 255

Trp Phe Gly Tyr Phe Asn Ser Thr Cys Asn Pro Leu Ile Tyr Gly Phe
            260                 265                 270

Phe Tyr Pro Trp Phe Arg Arg Ala Leu Lys Tyr Ile Leu Leu Gly Lys
        275                 280                 285

```
Ile Phe Ser Ser Cys Phe His Asn Thr Ile Leu Cys Met Gln Lys Glu
    290                 295                 300

Ser Glu
305
```